United States Patent
Cox et al.

(10) Patent No.: US 8,846,000 B2
(45) Date of Patent: Sep. 30, 2014

(54) RADIOLABELED PDE10 INHIBITORS

(75) Inventors: Christopher D. Cox, Harleysville, PA (US); Broc A. Flores, Boston, MA (US); Eric Hostetler, Collegeville, PA (US); Hong Fan, Lansdale, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 295 days.

(21) Appl. No.: 13/320,816

(22) PCT Filed: May 26, 2010

(86) PCT No.: PCT/US2010/036186
§ 371 (c)(1),
(2), (4) Date: Nov. 16, 2011

(87) PCT Pub. No.: WO2010/138577
PCT Pub. Date: Dec. 2, 2010

(65) Prior Publication Data
US 2012/0064005 A1    Mar. 15, 2012

Related U.S. Application Data

(60) Provisional application No. 61/182,149, filed on May 29, 2009.

(51) Int. Cl.
*A61K 51/00* (2006.01)
*A61M 36/14* (2006.01)

(52) U.S. Cl.
USPC .......... 424/1.11; 424/1.81; 250/362; 544/284

(58) Field of Classification Search
None
See application file for complete search history.

(56) References Cited

FOREIGN PATENT DOCUMENTS

| KR | 2009033634 A | * | 4/2009 |
|----|----|----|----|
| WO | WO9838187 | | 9/1998 |
| WO | WO2008020302 | | 2/2008 |
| WO | WO2010111432 | | 9/2010 |

OTHER PUBLICATIONS

Merrill et al. J. Labelled Cmpd. 1969, 346-350.*
Kulkarni et al. Indian J. Pharm. Sci. 1989, 201-203.*
Yu et al. J. Med. Chem. 1991, 34, 1505-1508.*
Zhang et al. Curr. Top. Med. Chem., 2007, 7, 1817-1828.*
Chang et al. Mol. Pharmacol. 1989, 803-808.*

* cited by examiner

*Primary Examiner* — Michael G. Hartley
*Assistant Examiner* — Sean R Donohue
(74) *Attorney, Agent, or Firm* — Sylvia A. Ayler; John C. Todaro

(57) ABSTRACT

The present invention is directed to radiolabeled pyrimidinone compounds of general structural formula I which are useful as radiotracers for quantitative imaging of PDE10 in mammals.

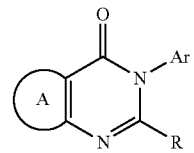

I

6 Claims, No Drawings

RADIOLABELED PDE10 INHIBITORS

CROSS REFERENCE TO RELATED APPLICATIONS

This application is the National Stage of International Application No. PCT/US2010/036186 filed on May 26, 2010, which claims the benefit under 35 U.S.C. 119(e) of U.S. Provisional Application No. 61/182,149, filed May 29, 2009.

FIELD OF THE INVENTION

The invention relates generally to novel PDE10 inhibitors and to their use as radiotracers for quantitative imaging of PDE10 in mammals.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds can be labeled with either positron or gamma emitting radionuclides. For imaging, the most commonly used positron emitting (PET) radionuclides are $^{11}C$, $^{18}F$, $^{15}O$ and $^{13}N$, all of which are accelerator produced, and have half lives of 20, 110, 2 and 10 minutes, respectively. Since the half-lives of these radionuclides are so short, it is only feasible to use them at institutions that have an accelerator on site or very close by for their production, thus limiting their use. Several gamma emitting radiotracers are available which can be used by essentially any hospital in the U.S. and in most hospitals worldwide. The most widely used of these are $^{99m}Tc$, $^{201}Tl$ and $^{123}I$.

In the last two decades, one of the most active areas of nuclear medicine research has been the development of receptor imaging radiotracers. These tracers bind with high affinity and specificity to selective receptors and neuroreceptors. Successful examples include radiotracers for imaging the following receptor systems: estrogen, muscarinic, dopamine D1 and D2, opiate, neuropeptide-Y, cannabinoid-1 and neurokinin-1.

Schizophrenia is debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., N. Engl. J. Med. (2005) 353: 1209-1223, citing the results of the Clinical Antipsychotic Trials of Intervention Effectiveness (CATIE).

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of PDE10 was reported by three groups independently and was distinguished from other PDEs on the basis of its amino acid sequence, functional properties, and tissue distribution (Fujishige et al., J. Biol. Chem. (1999) 274:18438-18445; Loughney et al., Gene (1999) 234: 109-117; Soderling et al., PNAS, USA (1999) 96: 7071-7076). The PDE10 subtype at present consists of a sole member, PDE10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PKA phosphorylation site that upon activation, i.e. PKA phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., Expert Opin. Ther. Patents (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions.

PET (Positron Emission Tomography) radiotracers and imaging technology may provide a powerful method for clinical evaluation and dose selection of PDE10 inhibitors. Thus, the invention herein is directed to radiolabeled PDE10 inhibitors that would be useful for exploratory and diagnostic imaging applications, both in vitro and in vivo, and for competition studies using radiolabeled and unlabeled PDE10 inhibitors.

SUMMARY OF THE INVENTION

The present invention is directed to pyrimidinone compounds of general structural and radiolabeled derivatives that are useful as therapeutic agents for the treatment of central nervous system disorders associated with phosphodiesterase 10 (PDE10). The present invention also relates to PDE10 inhibitors that are useful in treating neurological and psychiatric disorders and, in particular, schizophrenia, Huntington's disease, or psychosis associated with striatal hypofunction or basal ganglia dysfunction. The compounds of the invention are also directed to the use of radiolabeled PDE10 inhibitors via PET tracer technology for the in vivo quantitative imaging of PDE10 in mammals.

DETAILED DESCRIPTION OF THE INVENTION

The present invention is directed to PDE10 inhibitors and derivatives of structural formula I:

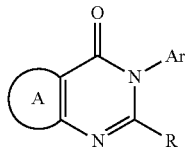

I or pharmaceutically acceptable salts and individual enantiomers and diasteromers thereof wherein:
A is selected from the group consisting of
(1) $C_{3-10}$ cycloalkyl,
(2) $C_{6-10}$ aryl,
(3) $C_{5-10}$ heteroaryl, and
(4) $C_{5-10}$ heterocyclyl;
wherein said cycloalkyl, aryl, heteroaryl, and heterocyclyl is each optionally substituted with 1 to 3 groups of $R^a$;
Ar is selected from the group consisting of
(1) —$(CH_2)_nC_{3-10}$ cycloalkyl,
(2) —$(O)_p(CH_2)_nC_{6-10}$ aryl,
(3) —$(CH_2)_nC_{5-10}$ heteroaryl, and
(4) —$(CH_2)_nC_{5-10}$ heterocyclyl,
wherein said cycloalkyl, aryl, heteroaryl, and heterocyclyl is each optionally substituted with 1 to 3 groups of $R^a$;
R is selected from the group consisting of
(1) —$(CH_2)_nC_{5-10}$ heteroaryl,
(2) —$(CH_2)_nC_{5-10}$ heterocyclyl,
(3) —$(CH_2)_nNR^2C(O)NR^2R^3$, and
(4) —$(CH_2)_nNR^2C(O)R^3$
wherein each is optionally substituted with 1 to 3 groups of $R^a$;
$R^2$ and $R^3$ are each independently selected from the group consisting of
(1) hydrogen,
(2) hydroxyl,
(3) —$C_{1-6}$ alkyl, which is unsubstituted or substituted with one or more halogen,
(4) —$(CH_2)_nF_3$,
(5) —$(CH_2)_nF$,
(6) —$C_{3-10}$ cycloalkyl,
(7) —$C_{6-10}$ aryl,
(8) —$C_5$-10 heteroaryl, and
(9) —$C_{5-10}$ heterocyclyl,
wherein said cycloalkyl, aryl, heterocyclyl, or heteroaryl is each optionally substituted with 1 to 3 groups of $R^a$;
$R^a$ is selected from the group consisting of
(1) halogen,
(2) hydroxyl,
(3) —$C_{1-6}$ alkyl, which is unsubstituted or substituted with one or more halogen,
(4) —$C_{3-6}$ cycloalkyl,
(5) —$NR^2C(O)R^2$,
(6) —$C(O)N(R^2)_2$,
(7) —$C(R^2)_2OR^2$,
(8) —$C(O)R^2$,
(9) $NO_2$,
(10) —CN,
(11) —$N(R^2)_2$,
(12) —$C(O)OR^2$,
(13) —$OR^2$,
(14) —$(CH_2)_nC_{5-10}$ heterocyclyl,
(15) —$(CH_2)_nC_{6-10}$ aryl, and
(16) —$(CH_2)_nC_{5-10}$ heteroaryl,
wherein said heterocyclyl, aryl, and heteroaryl are each optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl;
n is independently 0 to 4; and
p is independently 0 or 1; or a radiolabeled derivative and pharmaceutically acceptable salts thereof.

In a sub-embodiment $R^a$ is selected from the group consisting of
(1) halogen,
(2) hydroxyl,
(3) —$C_{1-6}$ alkyl, which is unsubstituted or substituted with one or more halogen,
(4) —CN,
(5) —$C(O)OR^2$,
(6) —$OR^2$,
(7) —$(CH_2)_nC_{5-10}$ heterocyclyl,
(8) —$(CH_2)_nC_{6-10}$ aryl, and
(9) —$(CH_2)_nC_{5-10}$ heteroaryl,
wherein said heterocyclyl, aryl, and heteroaryl are each optionally substituted with 1 to 3 groups of
(a) halogen,
(b) hydroxyl,
(c) —$C_{1-6}$ alkyl,
(d) —CN,
(e) —$(CH_2)_nCF_3$, and
(f) —$C_{6-10}$ aryl.

In another sub-embodiment, $R^a$ is selected from the group consisting of
(1) fluorine,
(2) chlorine,
(3) hydroxyl,
(4) -methyl, which is unsubstituted or substituted with one or more halogen,
(5) —CN,
(6) —C(O)O-t-butyl,
(7) methoxy,
(8) propoxy,
(9) phenyl,
(10) —$O(CH_2)_nF$,

(11) pyridyl, wherein said pyridyl is optionally substituted with 1 to 3 groups of
    (a) halogen,
    (b) hydroxyl,
    (c) —$C_{1-6}$ alkyl,
    (d) —CN,
    (e) —$(CH_2)_nCF_3$, or
    (f) —$C_{6-10}$ aryl.

An embodiment of the present invention includes compounds where A is —$(CH_2)_nC_{6-10}$ aryl optionally substituted with 1 to 3 groups of $R^a$ and all other variables are as previously described. Another embodiment of this invention is when said aryl is phenyl.

An embodiment of the present includes compounds where A is —$(CH_2)_nC_{5-10}$ heteroaryl optionally substituted with 1 to 3 groups of $R^a$ and all other variables are as previously described. Another embodiment of this invention is when said heteroaryl is pyridyl.

An embodiment of the present invention includes compounds where Ar is $(CH_2)_nC_{6-10}$ aryl optionally substituted with 1 to 3 groups of $R^a$ and all other variables are as previously described. Another embodiment of this invention is when said aryl is phenyl.

An embodiment of the present invention includes compounds where Ar is —$(CH_2)_nC_{5-10}$ heterocyclyl optionally substituted with 1 to 3 groups of $R^a$ and all other variables are as previously described. Another embodiment of this invention is when said heterocyclyl is selected from the group consisting of indole and indazole.

An embodiment of the present invention includes compounds where R is —$(CH_2)_nC_5$-10 heterocyclyl optionally substituted with 1 to 3 groups of $R^a$ and all other variables are as previously described. Another embodiment of this invention is when n is 1 to 3, preferably 2, and said heterocyclyl is selected from the group consisting of
    (a) indole, and
    (b) phthalimidyl.

An embodiment of the present invention includes compounds where R is —$(CH_2)_nNR^2C(O)NR^2R^3$ optionally substituted with 1 to 3 groups of $R^a$ and all other variables are as previously described. Another embodiment of this invention is when $R^2$ is hydrogen and $R^3$ is —$C_6$-$C_{10}$ aryl. Another embodiment of this invention is when said —$C_6$-$C_{10}$ aryl is biphenyl.

An embodiment of the present invention is where A and Ar is —$(CH_2)_nC_{6-10}$ aryl, each optionally substituted with 1 to 3 groups of $R^a$ and all other variables are as previously described.

An embodiment of this invention is where A and Ar is phenyl and R is —$(CH_2)_nC_{5-10}$ heterocyclyl, each optionally substituted with 1 to 3 groups of $R^a$ and all other variables are as previously described. Another embodiment of this invention is when n is 1 to 3, preferably 2, and said heterocyclyl is selected from the group consisting of
    (1) indole, and
    (2) phthalimidyl.

An embodiment of this invention is realized by structural formula IIa:

wherein:
Ar is selected from the group consisting of
    (1) phenyl,
    (2) indole,
    (3) indazole, and
    (4) biphenyl,
where each is optionally substituted with 1 to 3 groups of $R^a$ and all other variables are as previously described. Another embodiment of this invention is when R is —$(CH_2)_nC_{5-10}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
    (1) indole, and
    (2) phthalimidyl.

Another embodiment of the compound of formula IIa is where Ar is phenyl and R is —$(CH_2)_nC_{5-10}$ heterocyclyl or —$(CH_2)_n NR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
    (1) indole, and
    (2) phthalimidyl.

Another embodiment of the compound of formula IIa is where Ar is indole and R is —$(CH_2)_nC_{5-10}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
    (1) indole, and
    (2) phthalimidyl.

Another embodiment of the compound of formula IIa is where Ar is indazole and R is —$(CH_2)_nC_{5-10}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
    (1) indole, and
    (2) phthalimidyl.

Another embodiment of the compound of formula IIa is where Ar is biphenyl and R is —$(CH_2)_nC_{5-10}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
    (1) indole,
    (2) indole-dione,
    (3) isoindole, and
    (4) isoindole-dione.

In a sub-embodiment $R^a$ is selected from the group consisting of
    (1) halogen,
    (2) hydroxyl, (3) —$C_{1-6}$ alkyl, which is unsubstituted or substituted with one or more halogen,
(4) —CN,
(5) —$C(O)OR^2$,
(6) —$OR^2$,
(7) —$(CH_2)_nC_{5-10}$ heterocyclyl,
(8) —$(CH_2)_nC_{6-10}$ aryl, and
(9) —$(CH_2)_nC_{5-10}$ heteroaryl,
wherein said heterocyclyl, aryl, and heteroaryl are each optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl.

In another sub-embodiment, $R^a$ is selected from the group consisting of
(1) fluorine,
(2) chlorine,
(3) hydroxyl,
(4) -methyl, which is unsubstituted or substituted with one or more halogen,
(5) —CN,
(6) —C(O)O-t-butyl,
(7) methoxy,
(8) propoxy,
(9) phenyl,
(10) —$O(CH_2)_nF$, and
(11) pyridyl, wherein said pyridyl is optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl.

An embodiment of this invention is realized by structural formula IIb:

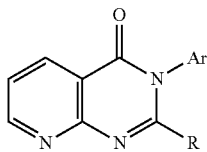

IIb wherein:
Ar is selected from the group consisting of
(1) phenyl,
(2) indole,
(3) indazole, and
(4) biphenyl
where each is optionally substituted with 1 to 3 groups of $R^a$ and all other variables are as previously described. Another embodiment of this invention is when R is —$(CH_2)_nC_{5-10}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
(1) indole, and
(2) phthalimidyl.

Another embodiment of the compound of formula III) is where Ar is phenyl and R is —$(CH_2)_nC_{5-10}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
(1) indole, and
(2) phthalimidyl.

Another embodiment of the compound of formula IIb is where Ar is indole and R is —$(CH_2)_nC_{5-40}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
(1) indole, and
(2) phthalimidyl.

Another embodiment of the compound of formula IIb is where Ar is indazole and R is —$(CH_2)_nC_{5-10}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
(1) indole, and
(2) phthalimidyl.

Another embodiment of the compound of formula IIb is where Ar is biphenyl and R is —$(CH_2)_nC_{5-10}$ heterocyclyl or —$(CH_2)_nNR^2C(O)NR^2R^3$ optionally substituted with 1 to 3 groups of $R^a$ and all other variables are as previously described. Still another embodiment of this invention is when n is 1 to 3, preferably 2, and said heterocyclyl is selected from the group consisting of
(1) indole, and
(2) phthalimidyl.

In a sub-embodiment $R^a$ is selected from the group consisting of
(1) halogen,
(2) hydroxyl,
(3) —$C_{1-6}$ alkyl, which is unsubstituted or substituted with one or more halogen,
(4) —CN,
(5) —$C(O)OR^2$,
(6) —$OR^2$,
(7) —$(CH_2)_nC_{5-10}$ heterocyclyl,
(8) —$(CH_2)_nC_{6-10}$ aryl, and
(9) —$(CH_2)_nC_{5-10}$ heteroaryl,
wherein said heterocyclyl, aryl, and heteroaryl are each optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl.

In another sub-embodiment, $R^a$ is selected from the group consisting of
(1) fluorine,
(2) chlorine,
(3) hydroxyl,
(4) -methyl, which is unsubstituted or substituted with one or more halogen,
(5) —CN,
(6) —C(O)O-t-butyl,
(7) methoxy,
(8) propoxy,
(9) phenyl,
(10) —$O(CH_2)_nF$, and

(11) pyridyl, wherein said pyridyl is optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl.

An embodiment of this invention is realized by structural formula IIIa:

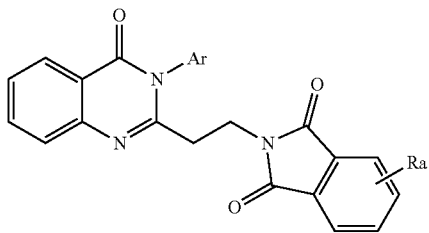

IIIa where Ar is selected from the group consisting of
(1) phenyl,
(2) indole,
(3) indazole, and
(4) biphenyl,
where each is optionally substituted with 1 to 3 groups of $R^a$ and all other variables are as previously described.

A sub-embodiment of this invention is realized when $R^a$ is selected from the group consisting of
(1) halogen,
(2) hydroxyl,
(3) —$C_{1-6}$ alkyl, which is unsubstituted or substituted with one or more halogen,
(4) —CN,
(5) —$C(O)OR^2$,
(6) —$OR^2$,
(7) —$(CH_2)_nC_{5-10}$ heterocyclyl,
(8) —$(CH_2)_nC_{6-10}$ aryl, and
(9) —$(CH_2)_nC_{5-10}$ heteroaryl,
wherein said heterocyclyl, aryl, and heteroaryl are each optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl.

In another sub-embodiment, $R^a$ is selected from the group consisting of
(1) fluorine,
(2) chlorine,
(3) hydroxyl,
(4) -methyl, which is unsubstituted or substituted with one or more halogen,
(5) —CN,
(6) —C(O)O-t-butyl,
(7) methoxy,
(8) propoxy,
(9) phenyl,
(10) —$O(CH_2)_nF$, and
(11) pyridyl, wherein said pyridyl is optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl.

An embodiment of this invention is realized by structural formula IIIb:

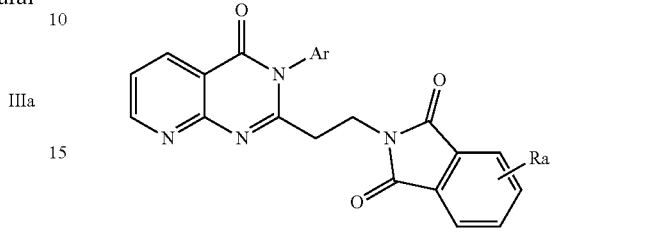

IIIb where Ar is selected from the group consisting of
(1) phenyl,
(2) indole,
(3) indazole, and
(4) biphenyl,
where each is optionally substituted with 1 to 3 groups of $R^a$ and all other variables are as previously described.

A sub-embodiment of this invention is realized when $R^a$ is selected from the group consisting of
(1) halogen,
(2) hydroxyl,
(3) —$C_{1-6}$ alkyl, which is unsubstituted or substituted with one or more halogen,
(4) —CN,
(5) —$C(O)OR^2$,
(6) —$OR^2$,
(7) —$(CH_2)_nC_{5-10}$ heterocyclyl,
(8) —$(CH_2)_nC_{6-10}$ aryl, and
(9) —$(CH_2)_nC_{5-10}$ heteroaryl,
wherein said heterocyclyl, aryl, and heteroaryl are each optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl.

In another sub-embodiment, $R^a$ is selected from the group consisting of
(1) fluorine,
(2) chlorine,
(3) hydroxyl,
(4) -methyl, which is unsubstituted or substituted with one or more halogen,
(5) —CN,
(6) —C(O)O-t-butyl,
(7) methoxy,
(8) propoxy,
(9) phenyl,
(10) —$O(CH_2)_nF$, and
(11) pyridyl, wherein said pyridyl is optionally substituted with 1 to 3 groups of
(a) halogen,
(b) hydroxyl,
(c) —$C_{1-6}$ alkyl,
(d) —CN,
(e) —$(CH_2)_nCF_3$, or
(f) —$C_{6-10}$ aryl.

In an embodiment, the invention is directed to radiolabeled compounds of formula I, IIa, IIb, IIIc or IIIb, for example $^{11}$C or $^{18}$F labeled compounds.

The present invention is also directed to a method for quantitative imaging of PDE10 in a mammal which comprises administering to a mammal in need of such imaging an effective amount of the radiolabeled compound of the present invention.

The present invention is also directed to a method for quantitative imaging of tissues bearing PDE10 in a mammal which comprises administering to a mammal in need of such imaging an effective amount of the radiolabeled compound of the present invention.

The present invention is also directed to a method for the quantitative imaging of PDE10 in tissues of a mammalian species which comprises administering to the mammalian species in need of such imaging an effective amount of the radiolabeled compound of the present invention.

The present invention is also directed to a method for quantitative imaging of PDE10 in the brain in a mammal which comprises administering to a mammal in need of such imaging an effective amount of the radiolabeled compound of the present invention.

In a specific embodiment the radiolabeled compounds and methods are for use in a human.

Examples of compounds of the invention made according to the schemes and Examples that follow include:

TABLE 1

| Cpd | Structure | Name | LRMS or HRMS m/z (M + H) |
|---|---|---|---|
| 1-1 | 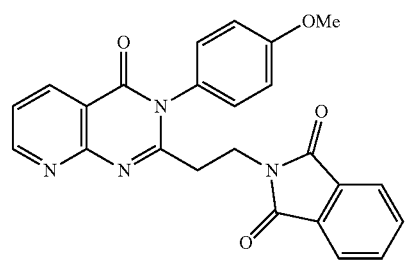 [SMILES: COc1ccc(-n2c(CCN3C(=O)c4ccccc4C3=O)nc3ncccc3c2=O)cc1] | 2-{2-[3-(4-methoxyphenyl)-4-oxo-3,4-dihydropyrido[2,3-d]pyrimidin-2-yl]ethyl}-1H-isoindole-1,3(2H)-dione | 427.1401 found, 427.1401 required. |
| 1-2 | 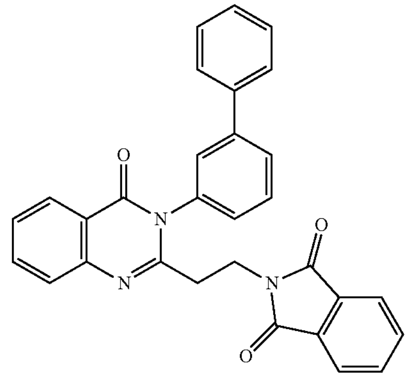 [SMILES: O=C1c2ccccc2C(=O)N1CCc1nc2ccccc2c(=O)n1-c1cccc(-c2ccccc2)c1] | 2-[2-(3-biphenyl-3-yl-4-oxo-3,4-dihydroquinazolin-2-yl)ethyl]-1H-isoindole-1,3(2H)-dione | 472 found, 472 required. |
| 1-3 | 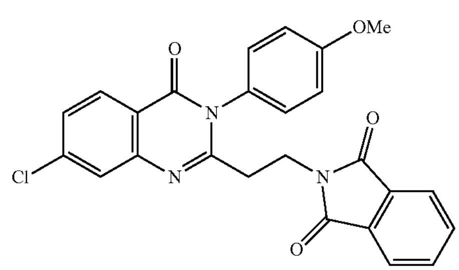 [SMILES: COc1ccc(-n2c(CCN3C(=O)c4ccccc4C3=O)nc3cc(Cl)ccc3c2=O)cc1] | 2-{2-[7-chloro-3-(4-methylphenyl)-4-oxo-3,4-dihydroquinazolin-2-yl]ethyl}-1H-isoindole-1,3(2H)-dione | 444 found, 444 required. |

TABLE 1-continued

| Cpd | Structure | Name | LRMS or HRMS m/z (M + H) |
|---|---|---|---|
| 1-4 | 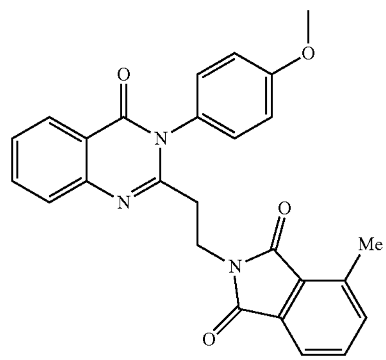 [SMILES: COc1ccc(-n2c(CCN3C(=O)c4cccc(C)c4C3=O)nc3ccccc3c2=O)cc1] | 2-{2-[3-(4-methoxyphenyl)-4-oxo-3,4-dihydroquinazolin-2-yl]ethyl}-4-methyl-1H-isoindole-1,3(2H)-dione | 440.1603 found, 440.1605 required. |
| 1-5 | 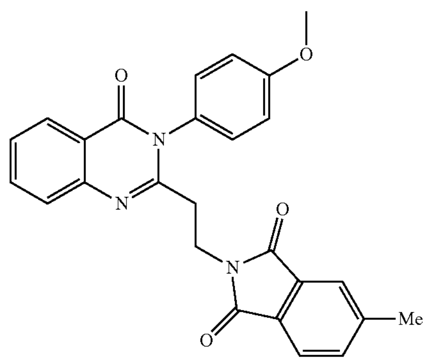 [SMILES: COc1ccc(-n2c(CCN3C(=O)c4ccc(C)cc4C3=O)nc3ccccc3c2=O)cc1] | 2-{2-[3-(4-methoxyphenyl)-4-oxo-3,4-dihydroquinazolin-2-yl]ethyl}-5-methyl-1H-isoindole-1,3(2H)-dione | 440.1600 found, 440.1605 required. |
| 1-6 | 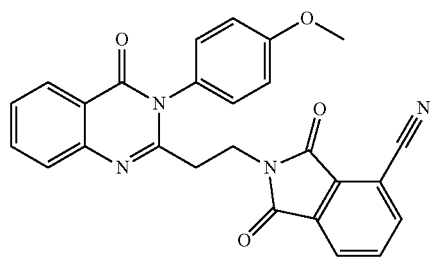 [SMILES: COc1ccc(-n2c(CCN3C(=O)c4cccc(C#N)c4C3=O)nc3ccccc3c2=O)cc1] | 2-{2-[3-(4-methoxyphenyl)-4-oxo-3,4-dihydroquinazolin-2-yl]ethyl}-1,3-dioxoisindoline-4-carbonitrile | 451.1411 found, 451.1401 required. |
| 1-7 | 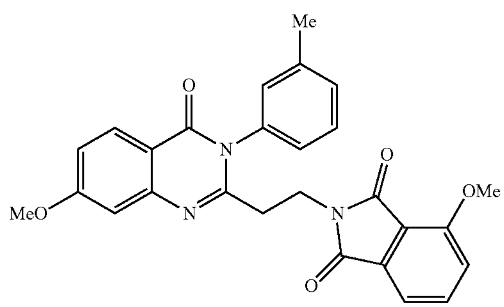 [SMILES: COc1ccc2c(=O)n(-c3cccc(C)c3)c(CCN3C(=O)c4cccc(OC)c4C3=O)nc2c1] | 4-methoxy-2-{2-[7-methoxy-3-(3-methylphenyl)-4-oxo-3,4-dihydroquinazolin-2-yl]ethyl}-1H-isoindole-1,3(2H)-dione | 470.1708 found, 470.1710 required. |
| 1-8 | 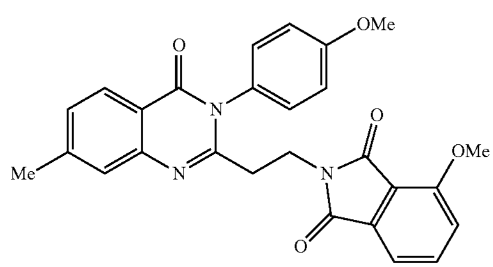 [SMILES: COc1ccc(-n2c(CCN3C(=O)c4cccc(OC)c4C3=O)nc3cc(C)ccc3c2=O)cc1] | 4-methoxy-2-{2-[3-(4-methoxyphenyl)-7-methyl-4-oxo-3,4-dihydroquinazolin-2-yl]ethyl}-1H-isoindole-1,3(2H)-dione | 470.1709 found, 470.1710 required. |

TABLE 1-continued

| Cpd | Structure | Name | LRMS or HRMS m/z (M + H) |
|---|---|---|---|
| 1-9 | 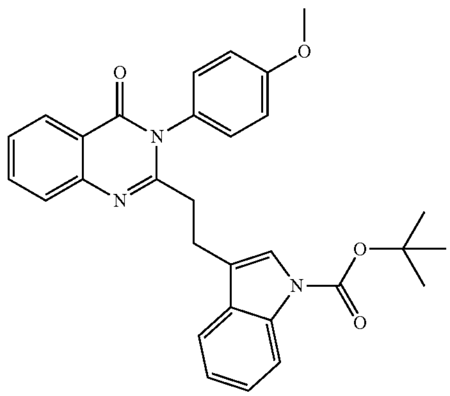 [SMILES: COc1ccc(-n2c(CCc3cn(C(=O)OC(C)(C)C)c4ccccc34)nc3ccccc3c2=O)cc1] | tert-butyl 3-{2-[3-(4-methoxyphenyl)-4-oxo-3,4-dihydroquinazolin-2-yl]ethyl}-1H-indole-1-carboxylate | 496.2242 found, 496.2231 required. |
| 1-10 | 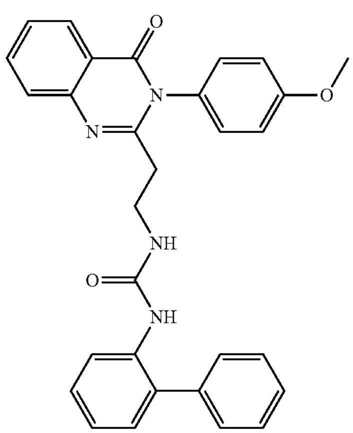 [SMILES: COc1ccc(-n2c(CCNC(=O)Nc3ccccc3-c3ccccc3)nc3ccccc3c2=O)cc1] | N-biphenyl-2-yl-N'-{2-[3-(4-methoxyphenyl)-4-oxo-3,4-dihydroquinazolin-2-yl]ethyl}urea | 490.6 found, 491.2 required. |
| 1-11 | 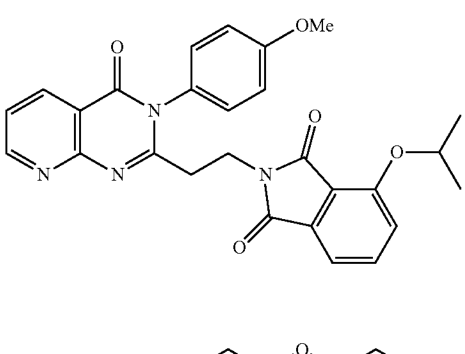 | 4-isopropoxy-2-{2-[3-(4-methoxyphenyl)-4-oxo-3,4-dihydropyrido[2,3-d]pyrimidin-2-yl]ethyl}-1H-isoindole-1,3(2H)-dione | 485.1830 found, 485.1819 required. |
| 1-12 | 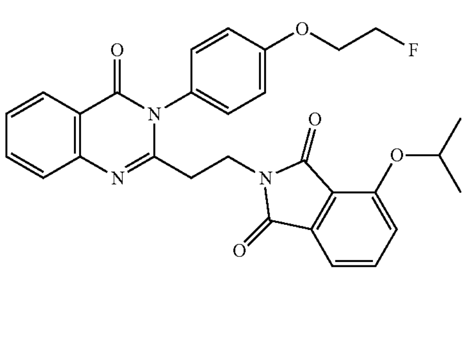 [SMILES: CC(C)Oc1cccc2c1C(=O)N(CCc1nc3ccccc3c(=O)n1-c1ccc(OCCF)cc1)C2=O] | 2-(2-{3-[4-(2-fluoroethoxy)phenyl]-4-oxo-3,4-dihydroquinazolin-2-yl}ethyl)-4-isopropoxy-1H-isoindole-1,3(2H)-dione | 516.1921 found, 516.1929 required. |

TABLE 1-continued

| Cpd | Structure | Name | LRMS or HRMS m/z (M + H) |
|---|---|---|---|
| 1-13 | 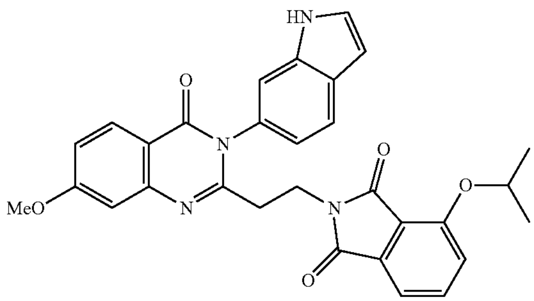 [SMILES: COc1ccc2c(=O)n(-c3ccc4cc[nH]c4c3)c(CCN3C(=O)c4cccc(OC(C)C)c4C3=O)nc2c1] | 2-{2-[3-(1H-indol-6-yl)-7-methoxy-4-oxo-3,4-dihydroquinazolin-2-yl]ethyl}-4-isopropoxy-1H-isoindole-1,3(2H)-dione | 523.1982 found, 523.1976 required. |
| 1-14 | 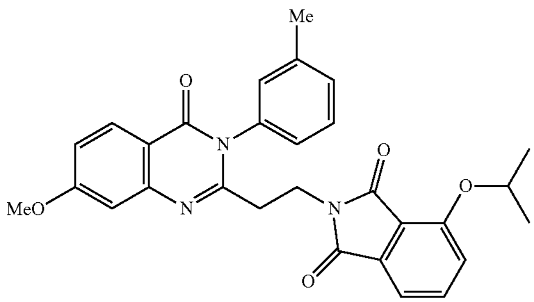 [SMILES: COc1ccc2c(=O)n(-c3cccc(C)c3)c(CCN3C(=O)c4cccc(OC(C)C)c4C3=O)nc2c1] | 4-isopropoxy-2-{2-[7-methoxy-3-(3-methylphenyl)-4-oxo-3,4-dihydroquinazolin-2-yl]ethyl}-1H-isoindole-1,3(2H)-dione | 498.2024 found, 498.2023 required. |
| 1-15 | 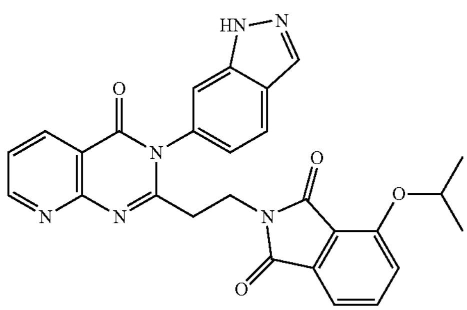 [SMILES: CC(C)Oc1cccc2c1C(=O)N(CCc1nc3ncccc3c(=O)n1-c1ccc3cn[nH]c3c1)C2=O] | 2-{2-[3-(1H-indazol-6-yl)-4-oxo-3,4-dihydropyrido[2,3-d]pyrimidin-2-yl]ethyl}-4-isopropoxy-1H-isoindole-1,3(2H)-dione | 495.1784 found, 495.1775 required. |
| 1-16 | 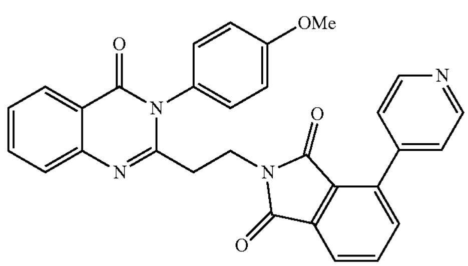 [SMILES: COc1ccc(-n2c(CCN3C(=O)c4cccc(-c5ccncc5)c4C3=O)nc3ccccc3c2=O)cc1] | 2-{2-[3-(4-methoxyphenyl)-4-oxo-3,4-dihydroquinazolin-2-yl]ethyl}-4-pyridin-4-yl-1H-isoindole-1,3(2H)-dione | 503.1707 found, 503.1714 required. |
| 1-17 | 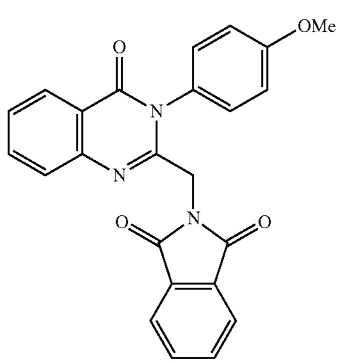 [SMILES: COc1ccc(-n2c(CN3C(=O)c4ccccc4C3=O)nc3ccccc3c2=O)cc1] | 2-{[3-(4-methoxyphenyl)-4-oxo-3,4-dihydroquinazolin-2-yl]methyl}-1H-isoindole-1,3(2H)-dione | 412.1292 found, 412.1292 required. |

TABLE 1-continued

| Cpd | Structure | Name | LRMS or HRMS m/z (M + H) |
|---|---|---|---|
| 1-18 | 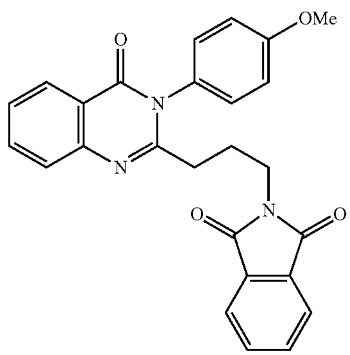 [SMILES: COc1ccc(-n2c(CCCN3C(=O)c4ccccc4C3=O)nc3ccccc3c2=O)cc1] | 2-{3-[3-(4-methoxyphenyl)-4-oxo-3,4-dihydroquinazolin-2-yl]propyl}-1H-isoindole-1,3(2H)-dione | 440.1592 found, 440.1605 required. |
| 1-19 | 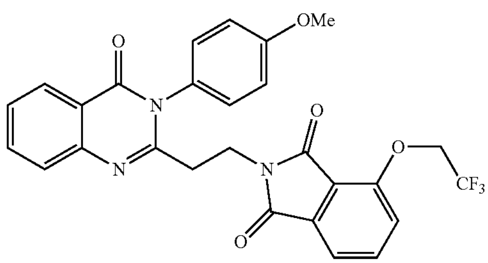 [SMILES: COc1ccc(-n2c(CCN3C(=O)c4cccc(OCC(F)(F)F)c4C3=O)nc3ccccc3c2=O)cc1] | 2-{2-[3-(4-methoxyphenyl)-4-oxo-3,4-dihydroquinazolin-2-yl]ethyl}-4-(2,2,2-trifluoroethoxy)-1H-isoindole-1,3(2H)-dione | 542.1419 found, 542.1428 required. |
| 1-20 | 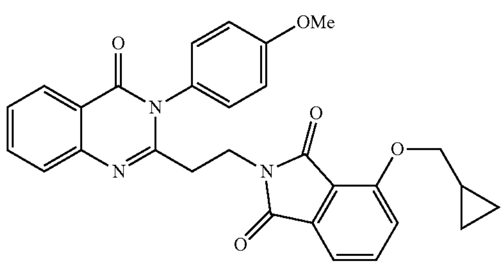 [SMILES: COc1ccc(-n2c(CCN3C(=O)c4cccc(OCC5CC5)c4C3=O)nc3ccccc3c2=O)cc1] | 4-(cyclopropylmethoxy)-2-{2-[3-(4-methoxyphenyl)-4-oxo-3,4-dihydroquinazolin-2-yl]ethyl}-1H-isoindole-1,3(2H)-dione | 496.1862 found, 496.1867 required. |
| 1-21 | 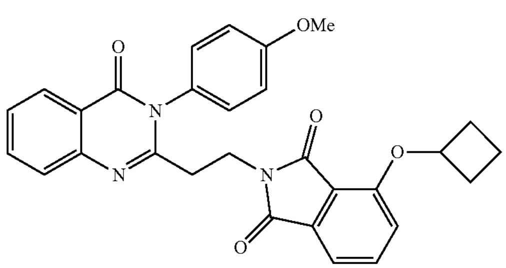 [SMILES: COc1ccc(-n2c(CCN3C(=O)c4cccc(OC5CCC5)c4C3=O)nc3ccccc3c2=O)cc1] | 4-(cyclobutyloxy)-2-{2-[3-(4-methoxyphenyl)-4-oxo-3,4-dihydroquinazolin-2-yl]ethyl}-1H-isoindole-1,3(2H)-dione | 496.1859 found, 496.1867 required. |
| 1-22 | 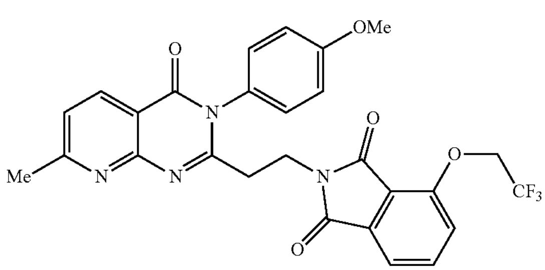 [SMILES: COc1ccc(-n2c(CCN3C(=O)c4cccc(OCC(F)(F)F)c4C3=O)nc3nc(C)ccc3c2=O)cc1] | 2-{2-[3-(4-methoxyphenyl)-7-methyl-4-oxo-3,4-dihydropyrido[2,3-d]pyrimidin-2-yl]ethyl}-4-(2,2,2-trifluoroethoxy)-1H-isoindole-1,3(2H)-dione | 539.1528 found, 539.1537 required. |

TABLE 1-continued

| Cpd | Structure | Name | LRMS or HRMS m/z (M + H) |
|---|---|---|---|
| 1-23 | 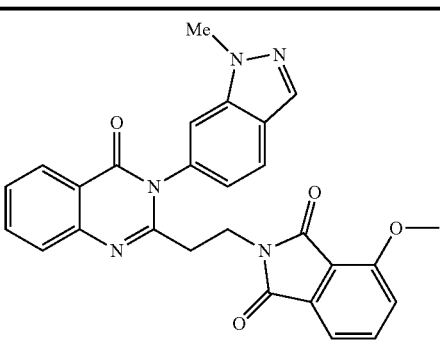 | 4-methoxy-2-{2-[3-(1-methyl-1H-indazol-6-yl)-4-oxo-3,4-dihydroquinazolin-2-yl]ethyl}-1H-isoindole-1,3(2H)-dione | 480.1656 found, 480.1666 required. |
| 1-24 | 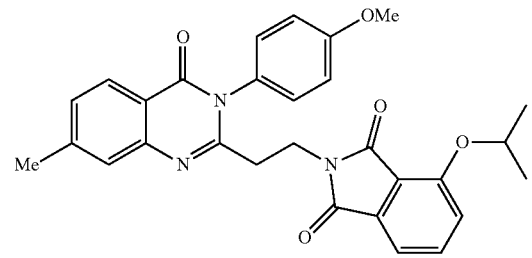 [SMILES: COc1ccc(-n2c(CCN3C(=O)c4cccc(OC(C)C)c4C3=O)nc3cc(C)ccc3c2=O)cc1] | 2-{2-[3-(4-methoxyphenyl)-7-methyl-4-oxo-3,4-dihydropyrido[2,3-d]pyrimidin-2-yl]ethyl}-4-(propan-2-yloxy)-1H-isoindole-1,3(2H)-one | 499.1973 found, 499.1976 required. |
| 1-25 | 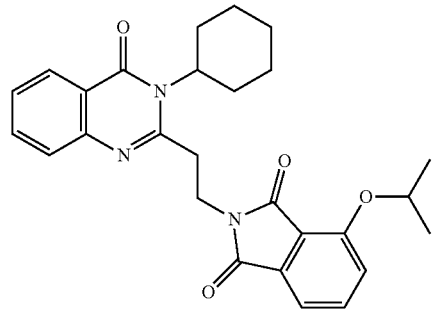 [SMILES: CC(C)Oc1cccc2c1C(=O)N(CCc1nc3ccccc3c(=O)n1C1CCCCC1)C2=O] | 2-[2-(3-cyclohexyl-4-oxo-3,4-dihyroquinazolin-2-yl)ethyl]-4-(propan-2-yloxy)-1H-isoindole-1,3(2H)-dione | 460.2231 found, 460.2238 required. | or a pharmaceutically acceptable salt, solvate or in vivo hydrolysable ester thereof.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

Specific embodiments of the present invention include a compound which is selected from the group consisting of the subject compounds of the Examples herein and pharmaceutically acceptable salts thereof and individual enantiomers and diastereomers thereof.

When any variable (e.g. aryl, heterocycle, $R^a$ etc.) occurs more than one time in any constituent, its definition on each occurrence is independent at every other occurrence. Also, combinations of substituents or variables are permissible only if such combinations result in stable compounds.

When $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C—C bond.

As used herein, "fluoroalkyl" refers to an alkyl substituent as described herein containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms.

The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. As used herein, the term "heteroaryl" refers to groups having 5 to 14 ring atoms, preferably 5, 6, 9, or 10 ring atoms; having 6, 10, or 14π electrons shared in a cyclic array; and having, in addition to carbon atoms, between one and about three heteroatoms selected from the group consisting of N, O, and S heteroaryl groups include, without limitation, thienyl, benzothienyl, furyl, benzofuryl, dibenzofuryl, pyrrolyl, imidazolyl, pyrazoiyl, pyridyl, pyrazinyl, pyrimidinyl, indolyl, quinolyl, isoquinolyl, quinoxalinyl, tetrazolyl, oxazolyl, thiazolyl, and isoxazolyl.

In certain other embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotnazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4-fluor-3-propylphenyl. As another non-limiting example, substituted n-octyls include 2,4-dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, arylalkylsulfnyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" refers to fluorine, chlorine, bromine and iodine.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

In an embodiment, the compounds of the present invention may be labeled as radiotracers for in vitro imaging. In another embodiment, the compounds of the invention may be prepared as Positron Emission Tomograph (PET) tracers for in vivo imaging and quantification of PDE10.

Suitable radionuclides that may be incorporated in the instant compounds include, but not limited, $^3H$ (also written as T), $^{11}C$, $^{18}F$, $^{35}S$, $^{125}I$, $^{82}Br$, $^{123}I$, $^{131}I$, $^{75}Br$, $^{15}O$, $^{13}N$, $^{211}At$ or $^{77}Br$. The radionuclide that is incorporated in the instant radiolabeled compounds will depend on the specific analytical or pharmaceutical application of that radiolabeled compound. Thus, for in vitro imaging of PDE10 and competition assays, compounds that incorporate $^3H$, $^{35}S$, $^{125}I$ or $^{82}Br$ will generally be most useful. For PET tracers, compounds that incorporate a radionuclide selected from $^{11}C$, $^{18}F$, $^{123}I$, $^{131}I$, $^{75}Br$, $^{76}Br$ or $^{77}Br$ are preferred. In certain applications incorporation of a chelating radionuclide such as $Tc^{99m}$ may also be useful. In other applications $^{18}F$ may be preferable over $^{11}C$ because with the longer half-life of $^{18}F$, imaging can be carried out long enough to allow a more specific signal to develop and improved conditions for receptor quantification studies. Compounds can be radiolabeled with either positron or gamma emitting radionuclides.

Radiolabeled PDE10 inhibitors, when labeled with the appropriate radionuclide, are potentially useful for a variety of in vitro and/or in vivo imaging applications. Specific examples of possible imaging applications include, but are not limited to, determining the location of, the relative activity of and/or quantifying PDE10, radioimmunoassays of PDE10 inhibitors, and autoradiography to determine the distribution of PDE10 in a mammal or an organ or tissue sample thereof. Using a fluorine-18 or carbon-11 labeled radiotracer that provides a PDE10-specific image in the brain and other tissues, the dose required to effectively inhibit the PDE10 enzyme can be determined by the blockade of the PET radiotracer image in humans.

In a specific embodiment, the instant radiolabeled PDE10 inhibitors when labeled with the positron emitting radionuclide, such as $^{11}C$, $^{18}F$, $^{15}O$ and $^{13}N$, are useful for positron emission tomographic (PET) imaging of PDE10 in the brain of living humans and experimental animals. These radiolabeled PDE10 inhibitors may be used as research tools to study the interaction of unlabeled PDE10 inhibitors with PDE10 in vivo via competition between the unlabeled drug and the radiolabeled compound for binding to the receptor. These types of quantitative studies are useful for determining the relationship between PDE10 occupancy and the dose of unlabeled PDE10 inhibitor, as well as for studying the duration of blockade of the receptor by various doses of the unlabeled PDE10 antagonist, agonists, and inverse agonists. As a clinical tool, the radiolabeled PDE10 inhibitors may be used to help define a clinically efficacious dose of a PDE10 inhibitor. In animal experiments, the radiolabeled PDE10 inhibitors can be used to provide information that is useful for choosing between potential drug candidates for selection for clinical development. The radiolabeled PDE10 inhibitors may also be used to study the regional distribution and concentration of PDE10 in the living human brain, as well as the brain of living experimental animals and in tissue samples. The radiolabeled PDE10 inhibitors may also be used to study disease or pharmacologically related changes in PDE10 concentrations.

In specific embodiments of the invention, PET tracers such as the present radiolabeled PDE10 inhibitors and currently available PET technology can be used, but is not limited to, to obtain the following information: relationship between level of receptor occupancy by candidate PDE10 inhibitors and clinical efficacy in patients; dose selection for clinical trials of PDE10 inhibitors prior to initiation of long term clinical studies; comparative potencies of structurally novel PDE10 inhibitors; investigating the influence of PDE10 inhibitors on in vivo transporter affinity and density during the treatment of clinical targets with PDE10 inhibitors and other agents; changes in the density and distribution of PDE10, for example, 1) during the active stage of a psychiatric disease or condition, 2) for the evaluation of efficacy during treatment, or 3) during remission; changes in PDE10 expression and distribution in CNS disorders; imaging neurodegenerative disease when PDE10 is upregulated; imaging neurodegenerative disease when PDE10 is involved; and the like.

Isotopically-labeled compounds of formula I, IIa, IIb, IIIa or IIIb can generally be prepared by conventional techniques known to those skilled in the art or by processes analogous to those described in the accompanying Examples using appropriate isotopically-labeled reagents in place of the non-labeled reagent previously employed to produce radiolabeled derivatives. In a particular embodiment, a compound of Formula I, IIa, or IIIa, 2-{2-[3-(4-hydroxyphenyl)-4-oxo-3,4-dihydroquinazolin-2-yl]ethyl}-4-isopropoxy-1H-isoindole-1,3(2H)-dione (D-6), can be labeled with $^{11}$C, to produce 4-isopropoxy-2-{2-[3-(4-$^{11}$C-methoxyphenyl)-4-oxo-3,4-dihydroquinazolin-2-yl]ethyl}-1H-isoindole-1,3(2H)-dione (E-1), which in turn can be used in PET studies. In another embodiment, a compound of Formula I, IIa, or IIIa, 2-{2-[3-(4-methoxyphenyl)-4-oxo-3,4-dihydroquinazolin-2-yl]ethyl}-4-pyridin-4-yl-1H-isoindole-1,3(2H)-dione, can be labeled and used in PET studies.

The radiolabeled PDE10 inhibitors of the present invention have utility in imaging PDE10 or for diagnostic imaging with respect to any of the mentioned neurological and psychiatric disorders associated with PDE10 dysfunction.

The present invention is also directed to a method for quantitative imaging of PDE10 in a mammal which comprises administering to a mammal in need of such quantitative imaging an effective amount of the radiolabeled compound of the present invention.

The present invention is also directed to a method for quantitative imaging of tissues bearing PDE10 in a mammal which comprises administering to a mammal in need of such quantitative imaging an effective amount of the radiolabeled compound of the present invention.

The present invention is also directed to a method for quantitative imaging of PDE10 in tissues of a mammalian species which comprises administering to the mammalian species in need of such quantitative imaging an effective amount of the radiolabeled compound of the present invention.

The present invention is also directed to a method for quantitative imaging of PDE10 in the brain in a mammal which comprises administering to a mammal in need of such quantitative imaging an effective amount of the radiolabeled compound of the present invention.

The present invention is further directed to a method for the detection or quantification of PDE10 in mammalian tissue which comprises administering to a mammal in which such quantification is desired an effective amount of the radiolabeled compound of the present invention.

In a specific embodiment of the methods of the present invention, the mammal is a human.

It will be understood that, as used herein, references to the compounds of structural formulas I, IIa, IIb, IIa, and IIIb are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupris and cuprous), ferric, ferrous, lithium, magnesium, manganese (manganic and manganous), potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

Accordingly, the pharmaceutical compositions of the present invention encompass any composition made by combining a compound of the present invention and a pharmaceutically acceptable carrier. By "pharmaceutically acceptable" it is meant the carrier, diluent or excipient must be compatible with the other ingredients of the formulation and not deleterious to the recipient thereof.

The pharmaceutical compositions of the present invention comprise compounds of the invention (or pharmaceutically acceptable salts thereof) as an active ingredient, a pharmaceutically acceptable carrier, and optionally one or more additional therapeutic agents or adjuvants. Such additional therapeutic agents can include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, xiv) neurontin (gabapentin), xv) pregabalin, and xvi) sodium channel blockers. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Exemplifying the invention are the specific compounds disclosed in the Examples and herein that can be used for treating a disease state or condition associated with a neurological or psychiatric disorder.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

The compounds of the invention are useful in methods of treating a neurological or psychiatric disorder associated with PDE10 dysfunction in a patient such as a mammal in need of such inhibition comprising the administration of an effective amount of the compound. In addition to primates, especially humans, a variety of other mammals can be treated according to the method of the present invention. The subject compounds are useful in a method of inhibiting PDE10 activity in a patient such as a mammal in need of such inhibition comprising the administration of an effective amount of the compound. In addition to primates, especially humans, a variety of other mammals can be treated according to the method of the present invention.

Applicants propose that inhibitors of PDE10 and, in particular inhibitors of PDE10A, will provide therapeutic benefit to those individuals suffering from psychiatric and cognitive disorders. The unique and exclusive distribution of PDE10A in the medium spiny projection neurons of the striatum, which four the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

As used herein, the term "'selective PDE10 inhibitor" refers to an organic molecule that effectively inhibits an enzyme from the PDE10 family to a greater extent than enzymes from the PDE 1-9 or PDE 11 families. In one embodiment, a selective PDE10 inhibitor is an organic molecule having a Ki for inhibition of PDE10 that is less than or about one-tenth that for a substance that is an inhibitor for another PDE enzyme. In other words, the organic molecule inhibits PDE10 activity to the same degree at a concentration of about one-tenth or less than the concentration required for any other PDE enzyme. Preferably, a selective PDE10 inhibitor is an organic molecule, having a Ki for inhibition of PDE10 that is less than or about one-hundredth that for a substance that is an inhibitor for another PDE enzyme. In other words, the organic molecule inhibits PDE10 activity to the same degree at a concentration of about one-hundredth or less than the concentration required for any other PDE enzyme. A "selective PDE10 inhibitor" can be identified, for example, by comparing the ability of an organic molecule to inhibit PDE10 activity to its ability to inhibit PDE enzymes from the other PDE families. For example, an organic molecule may be assayed for its ability to inhibit PDE10 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, and/or PDE11A.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temperal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the than "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In still other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

In still another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The present invention is further directed to a method for the manufacture of a medicament for treating neurological or psychiatric disorders associated with PDE10 dysfunction, including those disorders and conditions listed above, in humans and animals comprising combining a compound of the present invention with one or more additional therapeutic agents, carriers, or diluents.

The present invention is also directed to compounds of the invention for use in the treatment of neurological or psychiatric disorders associated with PDE10 dysfunction, including those disorders and conditions listed above, in humans and animals comprising combining a compound of the present invention with one or more additional therapeutic agents, carriers, or diluents.

The subject compounds are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. The terms "administration of" and or "administering a" compound should be understood to mean providing a compound of the invention or a prodrug of a compound of the invention to the individual in need of treatment.

When a compound of the present invention is used contemporaneously with one or more other drugs, a pharmaceutical composition in unit dosage form containing such other drugs and the compound of the present invention may be desirable. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art.

When the compounds of the invention are radiolabeled and/or are used as PET tracers, it is preferable that administration be done intravenously. Radiotracers labeled with positron emitting radionuclides are generally administered via intravenous injection within one hour of their synthesis due to the short half-life of the radionuclides involved, which is typically 20 and 110 minutes for C-11 and F-18, respectively. When the radiolabeled PDE10 inhibitors of the invention are administered to a human subject, the amount required for imaging will normally be determined by the prescribing physician with the dosage generally varying according to the quantity of emission from the radionuclide used. Those with ordinary skill in the art would appreciate that in most instances, an effective amount will be the amount of compound sufficient to produce emissions in the range of from about 1-5mCi. The mass associated with a PET tracer is in the form of the natural isotope, for example, $^{12}C$ for an $^{11}C$ PET tracer and $^{19}F$ for an $^{18}F$ PET tracer, respectively. This mass comprises from about 1 μg to about 50 μg of a radiolabeled PDE10 inhibitor in order to avoid significant inhibition of PDE10.

The following illustrative procedure may be utilized when performing PET imaging studies on patients in a clinical setting. The human subject is either unmedicated or premedicated with unlabeled PDE10 inhibitor or other pharmacological intervention some time prior to the day of the experiment and is fasted for at least 12 hours allowing water intake ad libitum. A 20 G two inch venous catheter is inserted into the contralateral ulnar vein for radiotracer administration. Administration of the PET tracer is often timed to coincide with time of maximum ($T_{max}$) or minimum ($T_{min}$) of PDE10 inhibitor (or other compound of intervention) concentration in the blood.

The human subject is positioned in the PET camera and a tracer dose of [$^{11}C$] Example 5 (<20 mCi) is administered via i.v. catheter. Either arterial or venous blood samples are taken at appropriate time intervals throughout the PET scan in order to analyze and quantitate the fraction of umetabolized [$^{11}C$] (Example 5) in plasma. Images are acquired for up to 120 minutes. Within ten minutes of the injection of radiotracer and at the end of the imaging session, 1 ml blood samples are obtained for determining the plasma concentration of any unlabeled PDE10 inhibitor (or other compound of intervention) which may have been administered before the PET tracer.

Tomographic images are obtained through image reconstruction. For determining the distribution of radiotracer, regions of interest (ROIs) are drawn on the reconstructed image including, but not limited to, the striatum, cerebellum and other specific brain regions or areas of the central nervous system. Radiotracer uptakes over time in these regions are used to generate time activity curves (TAC), including those obtained in the absence of any intervention or in the presence of PDE10 inhibitors or other compound of intervention at the various dosing paradigms examined. Data are expressed as radioactivity per unit time per unit volume (μCi/cc/mCi injected dose). TAC data are processed with various methods well-known in the field to yield quantitative parameters, such as Binding Potential (BP), that are proportional to the density of unoccupied PDE10. Inhibition of PDE10 is then calculated based on the change of BP in the presence of PDE10 inhibitors at the various dosing paradigms as compared to the BP in the unmedicated state. Inhibition curves are generated by plotting the above data vs the dose (concentration) of PDE10 inhibitors. The $ID_{50}$ values are obtained by curve fitting the dose-rate/inhibition curves with the following equation:

$$B = A_0 A_0 * I/(ID_{50}+I) + NS$$

where 13 is the %-Dose/g of radiotracer in tissues for each dose of clinical candidate, $A_0$ is the specifically bound radiotracer in a tissue in the absence of PDE10 inhibitors, I is the injected dose of antagonist, $ID_{50}$ is the dose of compound which inhibits 50% of specific radiotracer binding to PDE10, and NS is the amount of non-specifically bond radiotracer.

The subject compounds are further useful in a method for the prevention, treatment, control, amelioration, or reduction of risk of the diseases, disorders and conditions noted herein. The dose of the active ingredient in the composition may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets being adhered to by the patient, concurrent medication, and other factors which those skilled in the art will recognize. Generally, dosage levels between 0.01 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 mg of the active ingredient, such as, 1, 5, 10, 15, 20, 25, 50, 75, 100, 150, 200, 250, 300, 400, 500, 600, 750, 800, 900, and 1000 mg of the active ingredient for the symptomatic adjustment of the dosage to the patient to be treated. The compounds may be administered on a regimen of 1 to 4 times per day, preferably in a regimen of once or twice per day.

The compounds of the following examples had activity in inhibiting the human PDE10 enzyme as described in the biological assay that follows, generally with a Ki of less than about 1 µM. Many of the compounds within the present invention had activity in inhibiting the human PDE10 enzyme in the aforementioned assay, generally with a Ki of less than about 0.1 µM. Such a result is indicative of the intrinsic activity of the compounds in use as inhibitors of the PDE10 enzyme. In general, one of ordinary skill in the art would appreciate that a substance is considered to effectively inhibit PDE10 activity if it has a Ki of less than or about 1 µM, preferably less than or about 0.1 M. The present invention also includes compounds within the generic scope of the invention which possess activity as inhibitors of other phosphodiesterase enzymes.

In the table that follows, the PDE10 Ki is a measure of the ability of the test compound to inhibit the action of the PDE10 enzyme. To determine the selectivity of the test compounds for PDE10, the Ki of the compound was determined for PDEs 1-5, 7-9, and 11. In the table that follows, the selectivity is defined as the Ki of the test compound for the most potently inhibited PDE other than PDE10, divided by the Ki for PDE10. The PDE enzyme most potently inhibited other than PDE10 is listed.

TABLE 2

| Cpd | PDE10 Ki |
|---|---|
| A-1 | 87 nM |
| B-2 | 22 nM |
| B-3 | 2.0 nM |
| C-2 | 1.8 nM |
| D-5 | 0.83 nM |
| D-6 | 0.28 nM |
| D-7 | 0.15 nM |
| F-1 | 140 nM |
| G-1 | 0.10 nM |
| G-2 | 0.024 nM |
| 1-1 | 39 nM |
| 1-2 | 14 nM |
| 1-3 | 77 nM |
| 1-4 | 61 nM |
| 1-5 | 26 nM |
| 1-6 | 33 nM |
| 1-7 | 0.7 nM |
| 1-8 | 1.2 nM |
| 1-9 | 39 nM |
| 1-10 | 48 nM |
| 1-11 | 0.56 nM |
| 1-12 | 0.19 nM |
| 1-13 | 0.055 nM |
| 1-14 | 0.077 nM |
| 1-15 | 0.48 nM |

TABLE 2-continued

| Cpd | PDE10 Ki |
|---|---|
| 1-16 | 0.073 nM |
| 1-17 | 1900 nM |
| 1-18 | 219 nM |
| 1-19 | 0.79 nM |
| 1-20 | 1.3 nM |
| 1-21 | 1.0 nM |
| 1-22 | 2.08 nM |
| 1-23 | 0.95 nM |
| 1-24 | 0.10 nM |
| 1-25 | 11.0 nM |

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

EXAMPLES

The following abbreviations are used herein: Me: methyl; Et: ethyl; t-Bu: tert-butyl; Ar: aryl; Ph: phenyl; Bn: benzyl; Ac: acetyl; THF: tetrahydrofuran; DEAD: diethylazodicarboxylate; DIPEA: N,N-diisopropylethylamine; DMSO: dimethylsulfoxide; EDC: N-(3-Dimethylaminopropyl)-N'-ethylcarbodiimide; HOAT: 1-hydroxy-7-aza-benzotriazole; HOBT: hydroxybenzotriazole hydrate; Boc: tert-butyloxy carbonyl; $Et_3N$: triethylamine; DCM: dichloromethane; DCE: dichloroethane; BSA: bovine serum albumin; TFA: trifluoracetic acid; DMF: N,N-dimethylformamide; MTBE: methyl tert-butyl ether; $SOCl_2$: thionyl chloride; CDI: carbonyl diimidazole; rt: room temperature; HPLC: high performance liquid chromatography.

Several methods for preparing the compounds of this invention are illustrated in the following Schemes and Examples. Starting materials are made according to procedures known in the art or as illustrated herein. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes and examples may be varied to facilitate the reaction or to avoid unwanted reaction products.

The following examples are provided so that the invention might be more fully understood. These examples are illustrative only and should not be construed as limiting the invention in any way.

GENERAL SCHEMES

The subject compounds of the invention can be made according to the following general schemes. According to Scheme A, anthranilic acid (or alternatively a 1-amino-2-carboxy-heterocycle) can be coupled in one pot to an aliphatic carboxylic acid with triphenylphosphite, followed by addition of aniline (or an amino-substituted heterocycle) to provide compounds A-1 of the current invention.

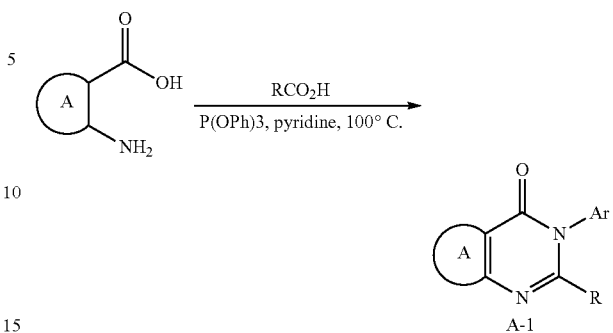

Scheme A

In Scheme B, if the R group of A-1 contains a phthalimide, it can be removed by refluxing in EtOH with hydrazine to provide primary amine B-1. This can be converted to substituted phthalimide B-2 by refluxing in dioxane with the appropriate phthalic anhydride. If B-2 contains a nucleophilic group (such as a phenol), it can be further functionalized by alkylation to provide B-3. If B-2 contains an arylbromide, it can be reacted under Suzuki or Stille conditions to provide B-4.

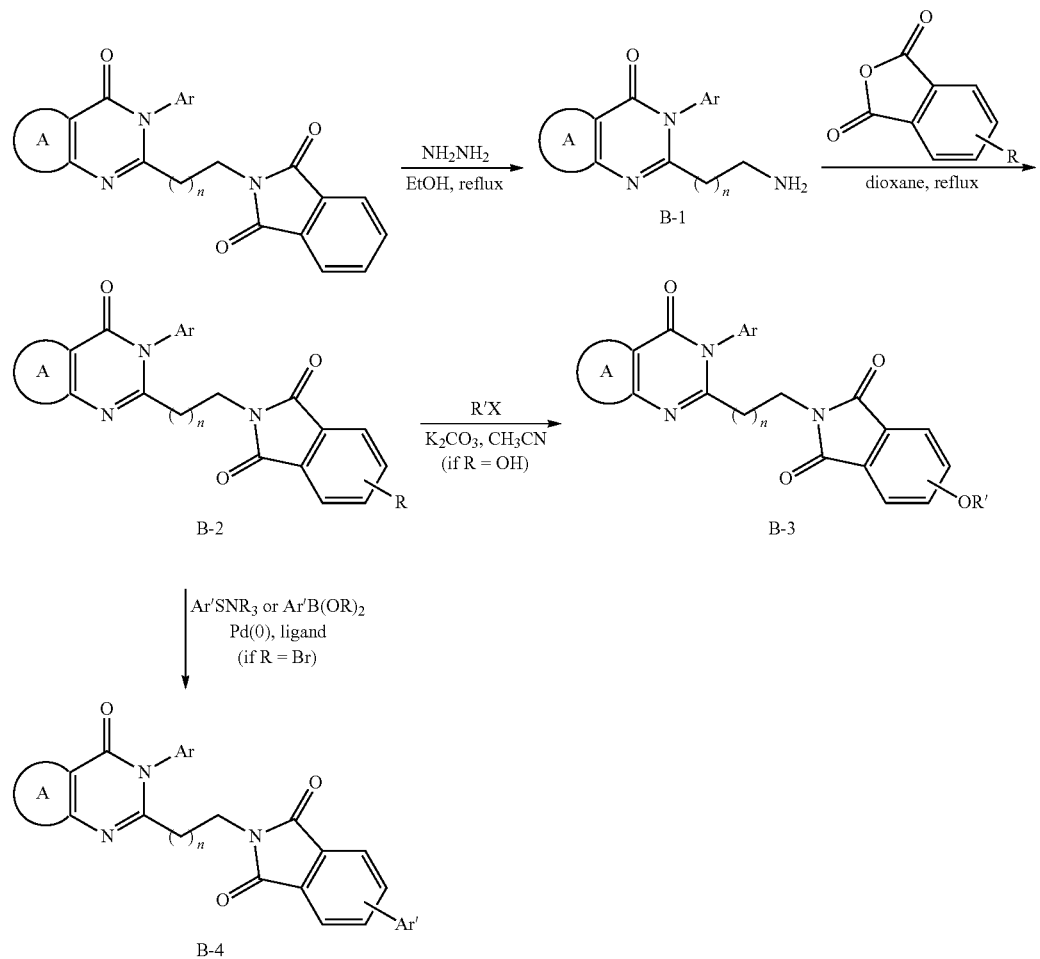

Scheme B

Example 1

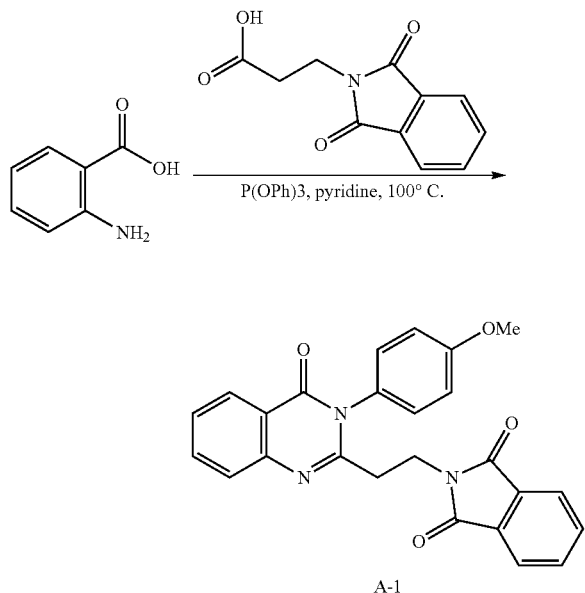

2-{2-[3-(4-methoxyphenyl)-4-oxo-3,4-dihydro-quinazolin-2-yl]ethyl}-1H-isoindole-1,3(2H)-dione (A-1)

Anthranilic acid (2.0 g, 14.6 mmol), 3-phthalimidopropionic acid (3.2 g, 14.6 mmol), and triphenylphosphite (4.0 mL, 15.3 mmol) were dissolved in pyridine (20 mL) and heated in a sealed tube at 100° C. for 2 hours. After cooling to room temperature, the tube was opened, p-anisidine (2.7 g, 21.9 mmol) was added and heating at 100° C. was resumed for 4 hours. The pyridine was removed by azeotroping with toluene, and the residue was suspended in $CHCl_3$ and toluene. The solids that crashed out were removed, and the residue was purified by silica gel chromatography with gradient elution (0 to 100% EtOAc in hexanes). A white solid precipitated from several of the fractions which was isolated by filtration to provide A-1 (2.23 g, 36%). Data for A-1: LRMS: calculated M+H for $C_{25}H_{19}N_3O_4$: 426.14. Found: 426.16.

Example 2

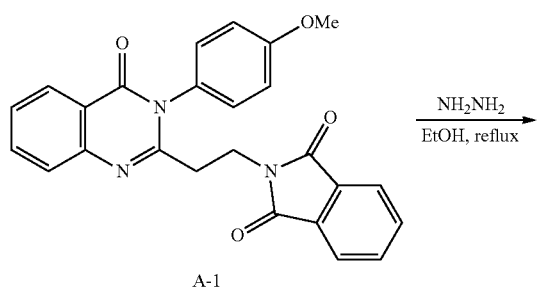

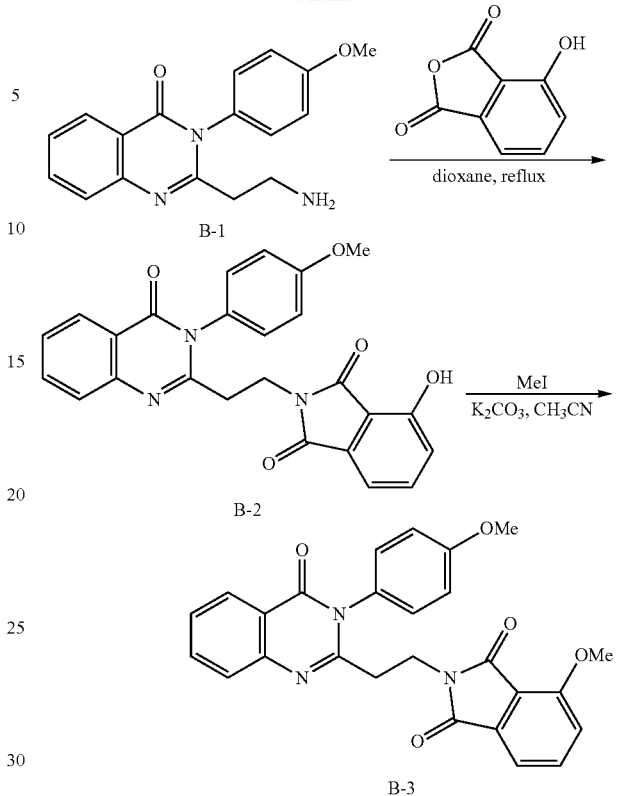

2-(2-aminoethyl)-3-(4-methoxyphenyl)quinazolin-4(3H)-one (B-1)

To a suspension of A-1 (2.23 g, 5.2 mmol) in EtOH (50 mL) was added hydrazine (495 μl, 15.7 mmol) and approximately 100 μL of water and the mixture was heated at reflux for 3 hours. After cooling to room temperature, the solids were removed and the filtrate was concentrated by rotary evaporation. The residue was suspended in EtOAc (150 mL) and the solids were again filtered. The filtrate was concentrated to provide B-1 (1.5 g, 97% yield) as a beige semi-solid. Data for B-1: LRMS: calculated M+H for $C_{17}H_{17}N_3O_2$: 296.13. Found: 296.25.

4-hydroxy-2-{2-[3-(4-methoxyphenyl)-4-oxo-3,4-dihydroquinazolin-2-yl]ethyl}-1H-isoindole-1,3(2H)-dione (B-2)

To a solution of B-1 (155 mg, 0.52 mmol) in 1,4-dioxane (2 mL) was added 3-hydroxyphthalic anhydride (86 mg, 0.52 mmol). The vial was sealed and heated to 80° C. overnight. The solvents were removed, the residue dissolved in $CHCl_3$, and purified by column chromatography (0 to 100% EtOAc in hexanes) to provide B-2 (135 mg, 58%) as a pale orange solid. Data for B-2: HRMS (ES) calculated M+H for $C_{25}H_{19}N_3O_5$: 442.1397. Found: 442.1394.

4-methoxy-2-{2-[3-(4-methoxyphenyl)-4-oxo-3,4-dihydroquinazolin-2-yl]ethyl}-1H-isoindole-1,3(2H)-dione (8-3)

To a solution of B-2 (39 mg, 0.088 mmol) in $CH_3CN$ (2 mL) was added $K_2CO_3$ (86 mg, 0.27 mmol) and iodomethane (8.3 μL, 0.14 mmol). The vial was sealed and heated at 65° C. for 1 hour. The solids were filtered off, the solvent removed, and the residue was dissolved in CHCl₃, and purified by column chromatography (0 to 100% EtOAc in hexanes) to provide B-3 (18 mg, 45%) as a white solid. Data for B-3: HRMS (ES) calculated M+H for $C_{26}H_{21}N_3O_5$: 456.1554. Found: 456.1554.

Example 3

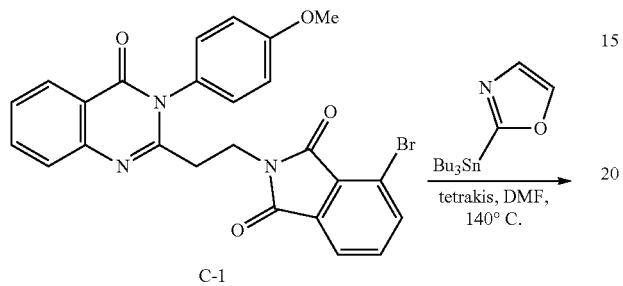

2-{2-[3-(4-methoxyphenyl)-4-oxo-3,4-dihydro-quinazolin-2-yl]ethyl}-4-(1,3-oxazol-2-yl)-1H-isoindole-1,3(2H)-dione (C-2)

A solution of C-1 (50 mg, 0.1 mmol), 2-(tri-n-butylstannyl)oxazole (43 mg, 0.12 mmol), and tetrakis(triphenylphosphine)palladium(0) (11.5 mg, 10 μmol) was sealed in a microwave vial and heated in a microwave reactor at 140° C. for 20 minutes. The residue was loaded directly onto a silica column and purified by column chromatography (0 to 100% EtOAc in hexanes) to provide C-2 (32 mg, 66%) as a colorless taffy. Data for C-2: HRMS (ES) calculated M+H for $C_{28}H_{20}N_4O_5$: 493.1506. Found: 493.1515.

Example 4

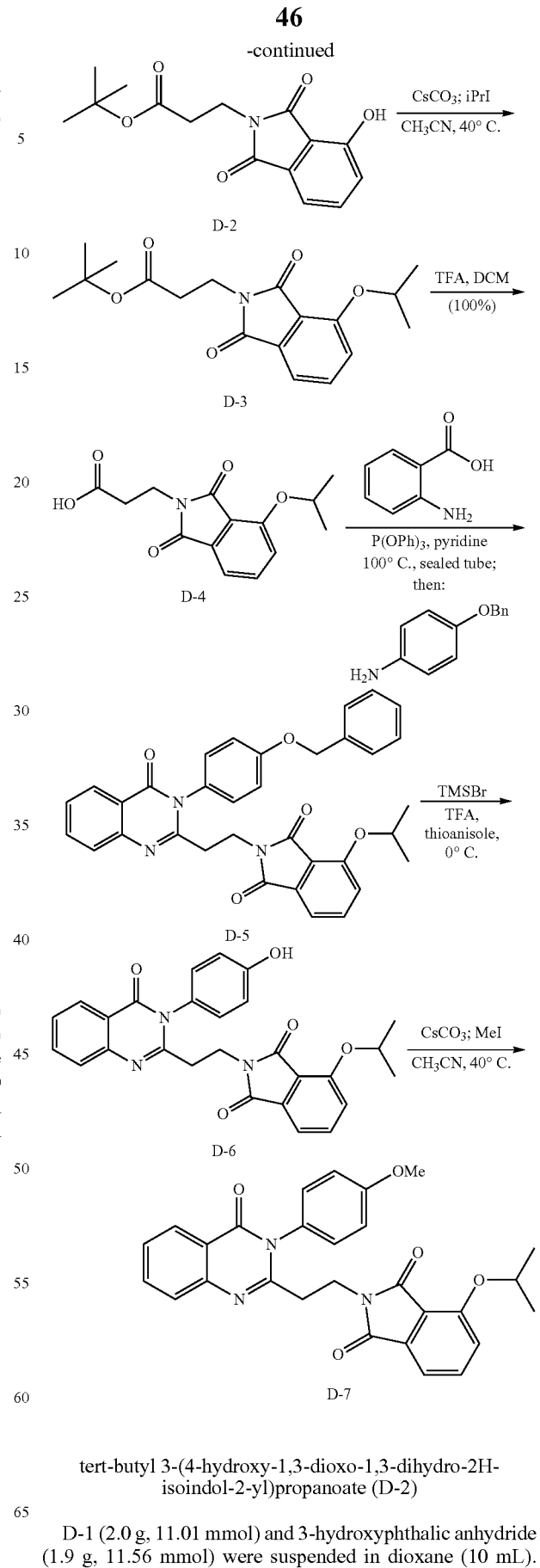

tert-butyl 3-(4-hydroxy-1,3-dioxo-1,3-dihydro-2H-isoindol-2-yl)propanoate (D-2)

D-1 (2.0 g, 11.01 mmol) and 3-hydroxyphthalic anhydride (1.9 g, 11.56 mmol) were suspended in dioxane (10 mL).

TEA (4.6 mL, 33 mmol) was added to the suspension and heated to 50° C. overnight. After cooling, the solution was diluted with EtOAc (150 mL) and washed with water (100 mL) and concentrated brine (100 mL). The organic layer was dried over $Na_2SO_4$ and concentrated to provide D-2 (2.1 g, 65.5% yield) as an off-white solid.

tert-butyl 3-(4-isopropoxy-1,3-dioxo-1,3-dihydro-2H-isoindol-2-yl)propanoate (D-3)

D-2 (1 g, 3.43 mmol) was suspended in acetonitrile (25 ml) in a sealed tube. While stirring, 2-iodopropane (687 μL, 6.87 mmol) and cesium carbonate (3.36 g, 10.30 mmol) were added. The tube was capped and heated to 80° C. for 4 hours. After cooling to room temperature, the reaction was diluted with EtOAc (150 mL) and washed with water (100 mL) and concentrated brine (100 mL). The organic layer was dried over $Na_2SO_4$ and concentrated to provide crude residue which was purified by column chromatography with gradient elution (0-100% EtOAc in Hexanes) to provide D-3 (835 g, 73.1%) as a white solid. Data for D-3: LRMS: calculated M+H for $C_{18}H_{23}NO_5$: 334.38. Found: 334.49.

3-(4-isopropoxy-1,3-dioxo-1,3-dihydro-2H-isoindol-2-yl)propanoic acid (D-4)

D-3 (835 g, 2.50 mmol) was dissolved in DCM (5 mL) and TFA (5 mL) and stirred at room temperature for 2 hours. Solvents were removed and the residue azeotroped with toluene. This provided D-4 (690 g, 100%) as an off-white solid. Data for D-4: LRMS: calculated M+H for $C_{14}H_{15}NO_5$: 278.27. Found: 278.62.

2-(2-{3-[4-(benzyloxy)phenyl]-4-oxo-3,4-dihydroquinazolin-2-yl}ethyl)-4-isopropoxy-1H-isoindole-1,3(2H)-dione (D-5)

Anthranilic acid (1.0 g, 7.29 mmol), D-4 (2.02 g, 7.29 mmol), and triphenylphosphite (2.01 mL, 7.66 mmol) were dissolved in pyridine (20 mL) and heated in a sealed tube at 100° C. for 2 hours. After cooling to room temperature, the tube was opened, 4-benzyloxyaniline hydrochloride (1.89 g, 8.02 mmol) was added and heating at 100° C. was resumed for 4 hours. The pyridine was removed by azeotroping with toluene, and the residue was suspended in $CHCl_3$ and toluene. The solids that crashed out were removed, and the residue was purified by silica gel chromatography with gradient elution (0 to 100% EtOAc in hexanes) to provide D-5 (1.9 g, 46%) as a white solid. Data for D-5: HRMS (ES) calculated M+H for $C_{34}H_{29}N_3O_5$: 560.2180. Found: 560.2195.

2-{2-[3-(4-hydroxyphenyl)-4-oxo-3,4-dihydroquinazolin-2-yl]ethyl}-4-isopropoxy-1H-isoindole-1,3(2H)-dione (D-6)

A solution of thioanisole (6 mL, 50.0 mmol) and bromotrimethylsilane (1.62 mL, 12.5 mmol) in TFA (10 mL) was prepared at 0° C. D-5 (1.4 g, 2.5 mmol) was added and stirred at 0° C. for 3 hours. The reaction was then warmed to room temperature and diluted with EtOAc (200 mL). After washing with 2 times with saturated $NaHCO_3$ (250 mL) followed by saturated brine (250 mL), the organic layer was dried over $Na_2SO_4$ and concentrated to provide crude residue. This was diluted with chloroform and purified by column chromatography with gradient elution (0 to 100% EtOAc in Hexanes) to provide D-6 (0.575 g, 49%) as a white solid. Data for D-6: HRMS (ES) calculated M+H for $C_{27}H_{23}N_3O_5$: 470.1710. Found: 470.1720.

4-isopropoxy-2-{2-[3-(4-methoxyphenyl)-4-oxo-3,4-dihydroquinazolin-2-yl]ethyl}-1H-isoindole-1,3(2H)-dione (D-7)

D-6 (35 mg, 0.075 mmol) was suspended in acetonitrile (2 ml) in a vial. While stirring, iodomethane (6.99 μL, 0.122 mmol) and cesium carbonate (73 mg, 0.224 mmol) were added. The vial was capped and heated to 80° C. for 4 hours. After cooling to room temperature, the reaction was diluted with EtOAc (30 mL), washed with water (25 mL), then brine (25 mL), dried over $Na_2SO_4$ and concentrated to provide crude material. This was diluted with chloroform and purified by column chromatography with gradient elution (0 to 100% EtOAc in Hexanes) to provide D-7 (28 mg, 76%) as a white solid. Data for D-7: HRMS (ES) calculated M+H for $C_{28}H_{25}N_3O_5$: 484.1867. Found: 484.1858.

Example 5

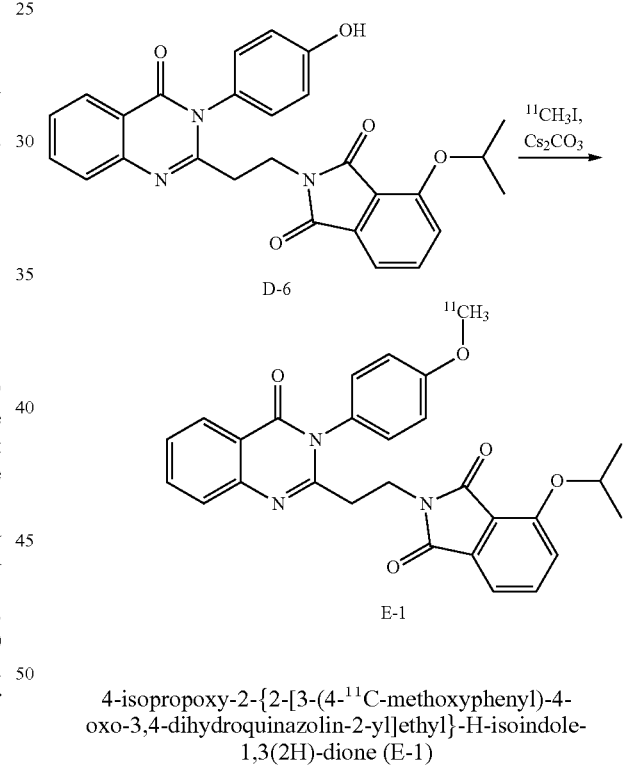

4-isopropoxy-2-{2-[3-(4-[$^{11}$C]-methoxyphenyl)-4-oxo-3,4-dihydroquinazolin-2-yl]ethyl}-H-isoindole-1,3(2H)-dione (E-1)

[$^{11}$C]$CO_2$ was provided by Siemens, North Wales, Pa. The [$^{11}$C]$CO_2$ was converted to [$^{11}$C]methyl iodide using a GE Medical Systems TRACERlab FXc system. Radiochemical procedures were carried out using a Gilson 233XL liquid handler. Radiotracers were purified by reverse-phase HPLC using a Waters 600E controller and the preparative HPLC runs were monitored at 254 nm using a Pharmacia-Biotech UV-MII UV detector and a Bioscan FlowCount photodiode detector. The radiochemical purities and identities were determined by co-injection with authentic standards on an analytical Waters 600E HPLC system equipped with a Waters 996 UV detector and a photodiode radiodetector (Bioscan FlowCount).

[$^{11}$C]Methyl iodide (300 mCi) was bubbled through a 0° C. mixture of D-6 (0.3-0.5 mg) in DMF (0.25 mL) containing $Cs_2CO_3$ (~1 mg). When the amount of trapped radioactivity peaked, the mixture was transferred to a vial preheated to 45° C. that contained $Cs_2CO_3$ (~0.5 mg). The reaction mixture was heated at 45° C. for 3 minutes, diluted with $H_2O$ (0.5 mL) and purified by HPLC (Phenomenex Gemini C18 column (10×150 mm, 5 μm), acetonitrile (solvent A) and 10 mM $Na_2HPO_4$ (solvent B) under 15-min linear gradient condition consisting of 50% A 50% B to 70% A 30% B at 5 ml/min. The peak corresponding to E-1 (retention time ~9 minutes) was collected in a heated rotoevaporator flask, most of the solvent was removed in vacuo, and the remainder was transferred to a sterile capped vial to give 56 mCi (19% uncorrected from [$^{11}$C]MeI) of E-1 with a specific activity of 3116 Ci/mmol (EOS) and a radiochemical and chemical purity>98%. The radiochemical and chemical purity was determined at 270 nm using a Waters XTerra C18 column (4.6×150 mm, 5 μm), isocratic 60% acetonitrile, 40% $H_2O$ (0.1% TFA) @ 1 mL/min, providing a retention time of 6 minutes for E-1. The specific activity was determined by counting an aliquot of E-t in a dose calibrator and determining the mass by analytical HPLC against a mass calibration curve for D-7.

Example 6

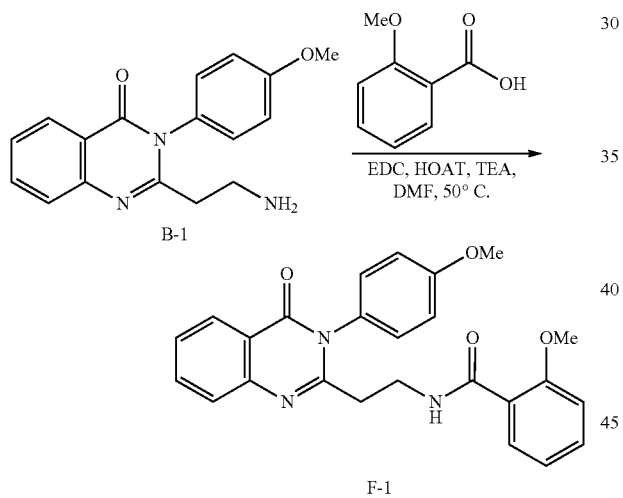

2-methoxy-N-{2-[3-(4-methoxyphenyl)-4-oxo-3,4-dihydroquinazolin-2-yl]ethyl}benzamide (F-1)

To a solution of B-1 (43 mg, 0.15 mmol) in 1 mL DMF was added 2-methoxybenzoic acid (27 mg, 0.18 mmol), HOAT (29 mg, 0.19 mmol), triethylamine (61 μL, 0.4 mmol), and EDC (34 mg, 0.18 mmol). The mixture was stirred at 40° C. for 3 hours, poured into EtOAc, washed with saturated aqueous $NaHCO_3$, washed twice with brine, dried over $Na_2SO_4$ and concentrated by rotary evaporation. The crude material was purified by reverse-phase HPLC (water/acetonitrile, 0.1% TFA), the fractions containing the product were basified with saturated aqueous $NaHCO_3$, extracted into EtOAc, washed with brine, dried over $Na_2SO_4$ and concentrated to provide F-1 as a colorless film. Data for F-1: HRMS (ES) calculated M+H for $C_{25}H_{23}N_3O_4$: 430.1761. Found: 430.1753.

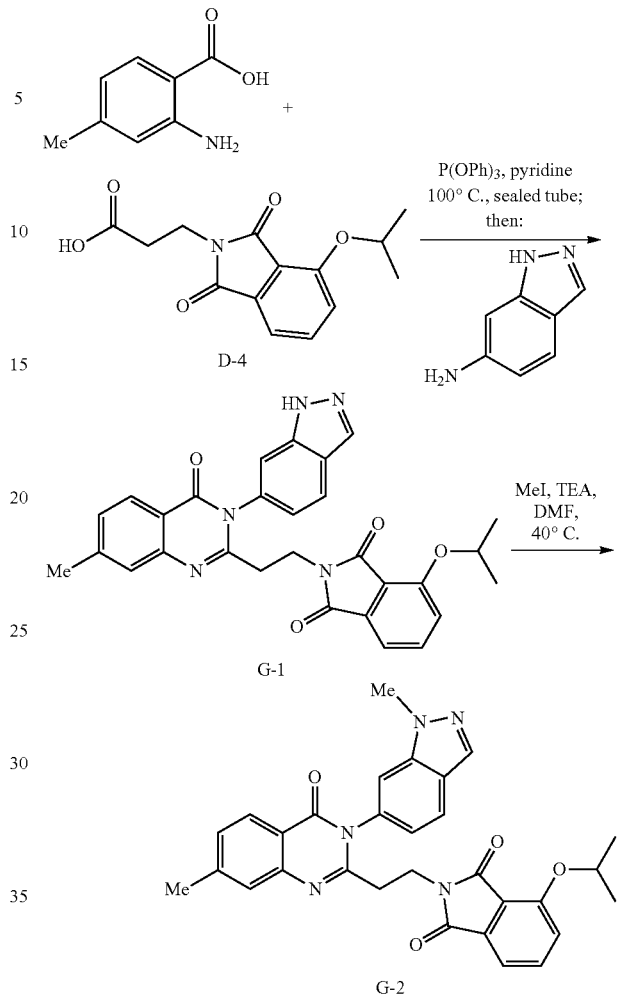

Example 7

2-{2-[3-(1H-indazol-6-yl)-7-methyl-4-oxo-3,4-dihydroquinazolin-2-yl]ethyl}-4-(propan-2-yloxy)-1H-isoindole-1,3(2H)-dione (G-1)

2-Amino-4-methylbenzoic acid (150 mg, 0.99 mmol), D-4 (275 mg, 0.99 mmol), and triphenylphosphite (286 μL, 1.1 mmol) were dissolved in 1 mL DMF, and heated in a sealed vial at 100° C. for 2 hours. After cooling to room temperature, the tube was opened, 6-aminoindazole (132 mg, 0.99 mmol) was added and heating at 100° C. was resumed for 4 hours. After cooling to room temperature, the reaction was partitioned between EtOAc and saturated $NaHCO_3$. After separation, the organic layer was washed with brine, dried over $Na_2SO_4$, and concentrated by rotary evaporation. The residue was purified by silica gel chromatography with gradient elution [0 to 100% 1:1 (EtOAc/20:1:1 EtOH/$NH_4OH$/$H_2O$) in hexanes] to provide G-1 (302 mg, 60%) as a brown solid. Data for G-1: HRMS (ES) calculated M+H for $C_{29}H_{25}N_5O_4$: 508.1979. Found: 508.1983.

2-{2-[7-methyl-3-(1-methyl-1H-indazol-6-yl)-4-oxo-3,4-dihydroquinazolin-2-yl]ethyl}-4-(propan-2-yloxy)-1H-isoindole-1,3(2H)-dione (G-2)

A solution of G-1 (150 mg, 0.30 mmol), iodomethane (18.5 μL, 0.3 mmol) and triethylamine (excess) in 1 mL of DMF was heated at 40° C. for several hours. The crude reaction was purified by reverse phase chromatography (CH₃ CN/H₂O plus TFA as modifier) to provide G-2 (26 mg, 34%), the first eluting regioisomer, as a white solid. Data for G-2: LC/MS: rt=1.3 min; m/z (M+H)=522.4. ¹H NMR (500 MHz, CDCl₃): d 8.15 (m, 1H), 8.05 (m, 1H), 7.85 (m, 1H), 7.55 (m, 1H), 7.4-7.25 (m, 4H), 7.15 (m, 1H), 7.05 (m, 1H), 4.7 (m, 1H), 4.1 (m, 2H), 4.1 (s, 3H), 2.75 (m, 2H), 2.5 (s, 3H), 1.4 (dd, 6H) ppm.

Example 8

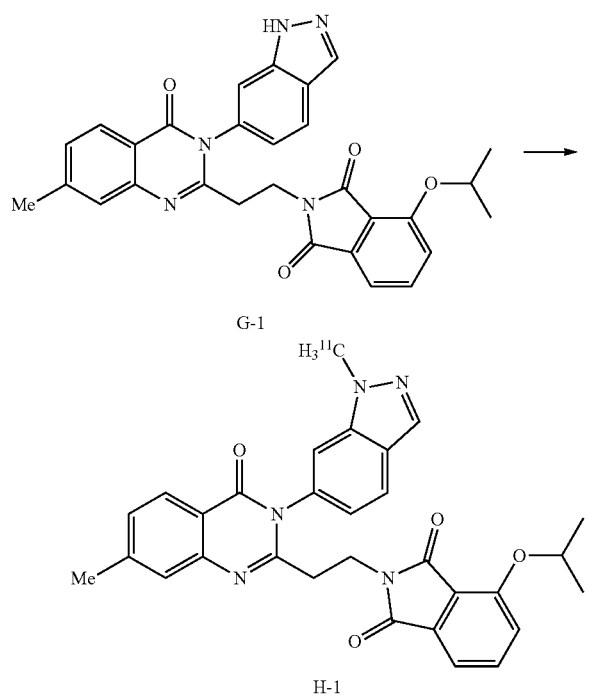

2-{2-[7-methyl-3-(1-¹¹C-methyl-1H-indazol-6-yl)-4-oxo-3,4-dihydroquinazolin-2-yl]ethyl}-4-(propan-2-yloxy)-1H-isoindole-1,3(2H)-dione (H-1)

[¹¹C]Methyl iodide was converted to [¹¹C]methyl triflate by distillation through a column (~5×30 mm) of silver triflate heated to 200° C. The [¹¹C]methyl triflate was bubbled into mixture of G-1 (0.2-0.5 mg) in DMF (0.25 mL) containing 1M sodium hydroxide (3 uL) at room temperature. When the amount of radioactivity trapped in solution peaked, the mixture was allowed to set at room temperature for 3 min. The reaction mixture was then diluted with H₂O (0.5 mL) and purified by HPLC (Phenomenex Synergi Polar-RP 10×150 mm, 5 μm), using acetonitrile (solvent A) and 0.1% trifluoracetic acid in water (solvent B) under isocratic conditions of 55% A 45% B at 5 ml/min. The peak corresponding to H-1 (retention time ~10 minutes) was collected in a flask, most of the solvent was removed in vacuo, and the remainder was transferred to a sterile capped vial to give 58 mCi (31% yield by integration of HPLC chromatogram) of H-1 with a specific activity of 2039 Ci/mmol (EOS) and a radiochemical purity>98%.

Example 9

Biological Example

Florescence Polarization Assay

The activity of the compounds in accordance with the present invention as PDE10 inhibitors may be readily determined without undue experimentation using a fluorescence polarization (FP) methodology well known in the art (Huang, W., et al., *J. Biomol Screen*, 2002, 7: 215). In particular, the compounds of the Examples had activity in reference assays by exhibiting their ability to inhibit the hydrolysis of the phosphate ester bond of a cyclic nucleotide. Any compound exhibiting a Ki (inhibitory constant) below 1 μM would be considered a PDE10 inhibitor as defined herein.

In a typical experiment the PDE10 inhibitory activity of the compounds of the present invention was determined in accordance with the following experimental method. PDE10A2 was amplified from human fetal brain cDNA (Clontech, Mountain View, Calif.) using a forward primer corresponding to nucleotides 56-77 of human PDE10A2 (Accession No. AF127480, Genbank Identifier 4894716), containing a Kozak consensus sequence, and a reverse primer Corresponding to nucleotides 2406-2413 of human PDE100A2 (Accession No. AF127480, Genbank Identifier 4894716). Amplification with Easy-A polymerase (Stratagene, La Jolla, Calif.) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, Calif.) according to standard protocol.

AD293 cells with 70-80% confluency were transiently transfected with human PDE10A2/pcDNA3.2-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE100A2 activity.

The fluorescence polarization assay for cyclic nucleotide phosphodiesterases was performed using an IMAP® FP kit supplied by Molecular Devices, Sunnyvale, Calif. (product #R8139). IMAP® technology has been applied previously to phosphodiesterase assays (Huang, W., et al., *J. Biomol Screen*, 2002, 7: 215). Assays were performed at room temperature in 384-well microtiter plates with an incubation volume of 20.2 μL. Solutions of test compounds were prepared in DMSO and serially diluted with DMSO to yield 8 μL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. *Neuropharmacology* (2006) 51:386-396; Becker, et al. *Behav Brain Res* (2008) 186(2):155-60; Threlfell, et al., *J Pharmacol Exp Ther* (2009) 328(3):785-795), 2-{4-[pyridin-4-yl-1-(2,2,2-trifluoroethyl)-1H-pyrazol-3-yl]phenoxymethyl}quinoline succinic acid or 2-[4-(1-methyl-4-pyridin-4-yl-1H-pyrazol-3-yl)-phenoxymethyl]quinoline succinic acid (see Schmidt, et al. *J Pharmacol Exp Ther* (2008) 325:681-690; Threlfell, et al., *J Pharmacol Exp Ther* (2009) 328(3): 785-795). 0% of inhibition is determined by using DMSO (1% final concentrations).

A Labcyte Echo 555 (Labcyte, Sunnyvale, Calif.) is used to dispense 200 mL from each well of the titration plate to the 384 well assay plate. A solution of enzyme (1/1600 dilution from aliquots; sufficient to produce 20% substrate conversion) and a separate solution of FAM-labeled cAMP PDE from Molecular Devices (product #R7506), at a final concentration of 50 nM are made in the assay buffer (10 mM Tris HCl, pH 7.2, 10 mM MgCl$_2$, 0.05% NaN$_3$ 0.01% Tween-20, and 1 mM DTT). The enzyme and the substrate are then added to the assay plates in two consecutive additions of 10 μL, and then shaken to mix. The reaction is allowed to proceed at room temperature for 30 minutes. A binding solution is then made from the kit components, comprised of 80% Solution A, 20% Solution B and binding reagent at a volume of 1/600 the total binding solution. The enzymatic reaction is stopped by addition of 60 μL of the binding solution to each well of the assay plates and the plates are sealed and shaken for 10 seconds. The plate was incubated at room temperature for at least one hour prior to determining the fluorescence polarization (FP).

The parallel and perpendicular fluorescence of each well of the plate was measured using a Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization($mP$)=1000*($S/So-P/Po$)/($S/So+P/Po$).

Dose-inhibition profiles for each compound were characterized by fitting the mP data to a four-parameter equation given below. The apparent inhibition constant (KI), the maximum inhibition at the low plateau relative to "100% Inhibition Control" (Imax; e.g. 1=>same as this control), the minimum inhibition at the high plateau relative to the "0% Inhibition Control" (1 min, e.g. 0=> same as the no drug control) and the Hill slope (nH) are determined by a non-linear least squares fitting of the mP values as a function of dose of the compound using an in-house software PROGRAM based on the procedures described by Mosser et al., *JALA*, 2003, 8: 54-63, using the following equation:

$$mP = \frac{(0\%\ mP - 100\%\ mP)(I\max - I\min)}{1 + \left[\left(10^{-pK_I}\left(1 + \frac{[\text{Substrate}]}{K_M}\right)\right)\right]^{nH}} + 100\%\ mP + (0\%\ mP - 100\%\ mP)(1 - I\max)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Example 10

Biological Example

Selectivity Assay

Selectivity for PDE10, as compared to other PDE families, was also assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 μL. Solutions of test compounds were prepared in DMSO and serially diluted with DMSO to yield 30 μL of each often solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product #R7506 or cGMP#R7508), at a final concentration of 50 nM were made in the assay buffer (10 mM Tris HCl, pH 7.2, 10 mM MgCl$_2$, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 μL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 μL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland).

The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A 1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM.

What is claimed:
1. A radiolabeled compound which is
2-{2-[3-(4-methoxyphenyl)-4-oxo-3,4-dihydropyrido[2,3-d]pyrimidin-2-yl]ethyl}-1H-isoindole-1,3(2H)-dione,
2-[2-(3-biphenyl-3-yl-4-oxo-3,4-dihydroquinazolin-2-yl)ethyl]-1H-isoindole-1,3(2H)-dione,
2-{2-[7-chloro-3-(4-methylphenyl)-4-oxo-3,4-dihydroquinazolin-2-yl]ethyl}-1H-isoindole-1,3(2H)-dione,
2-{2-[3-(4-methoxyphenyl)-4-oxo-3,4-dihydroquinazolin-2-yl]ethyl}-4-methyl-1H-isoindole-1,3(2H)-dione,
2-{2-[3-(4-methoxyphenyl)-4-oxo-3,4-dihydroquinazolin-2-yl]ethyl}-5-methyl-1H-isoindole-1,3(2H)-dione,
2-{2-[3-(4-methoxyphenyl)-4-oxo-3,4-dihydroquinazolin-2-yl]ethyl}-1,3-dioxoisoindoline-4-carbonitrile,

4-methoxy-2-{2-[7-methoxy-3-(3-methylphenyl)-4-oxo-3,4-dihydroquinazolin-2-yl]ethyl}-1H-isoindole-1,3(2H)-dione,
4-methoxy-2-{2-[3-(4-methoxyphenyl)-7-methyl-4-oxo-3,4-dihydroquinazolin-2-yl]ethyl}-1H-isoindole-1,3(2H)-dione,
tert-butyl 3-{2-[3-(4-methoxyphenyl)-4-oxo-3,4-dihydroquinazolin-2-yl]ethyl}-1H-indole-1-carboxylate,
N-biphenyl-2-yl-N'-{2-[3-(4-methoxyphenyl)-4-oxo-3,4-dihydroquinazolin-2-yl]ethyl}urea,
4-isopropoxy-2-{2-[3-(4-methoxyphenyl)-4-oxo-3,4-dihydropyrido[2,3-d]pyrimidin-2-yl]ethyl}-1H-isoindole-1,3(2H)-dione,
2-(2-{3-[4-(2-fluoroethoxy)phenyl]-4-oxo-3,4-dihydroquinazolin-2-yl}ethyl)-4-isopropoxy-1H-isoindole-1,3(2H)-dione,
2-{2-[3-(1H-indol-6-yl)-7-methoxy-4-oxo-3,4-dihydroquinazolin-2-yl]ethyl}-4-isopropoxy-1H-isoindole-1,3(2H)-dione,
4-isopropoxy-2-{2-[7-methoxy-3-(3-methylphenyl)-4-oxo-3,4-dihydroquinazolin-2-yl]ethyl}-1H-isoindole-1,3(2H)-dione,
2-{2-[3-(1H-indazol-6-yl)-4-oxo-3,4-dihydropyrido[2,3-d]pyrimidin-2-yl]ethyl}-4-isopropoxy-1H-isoindole-1,3(2H)-dione,
2-{2-[3-(4-methoxyphenyl)-4-oxo-3,4-dihydroquinazolin-2-yl]ethyl}-4-pyridin-4-yl-1H-isoindole-1,3(2H)-dione,
2-{[3-(4-methoxyphenyl)-4-oxo-3,4-dihydroquinazolin-2-yl]methyl}-1H-isoindole-1,3(2H)-dione,
2-{3-[3-(4-methoxyphenyl)-4-oxo-3,4-dihydroquinazolin-2-yl]propyl}-1H-isoindole-1,3(2H)-dione,
2-{3-[3-(4-methoxyphenyl)-4-oxo-3,4-dihydroquinazolin-2-yl]ethyl}-4-(2,2,2-trifluoroethoxy)-1H-isoindole-1,3(2H)-dione,
4-(cyclopropylmethoxy)-2-{2-[3-(4-methoxyphenyl)-4-oxo-3,4-dihydroquinazolin-2-yl]ethyl}-1H-isoindole-1,3(2H)-dione,
4-(cyclobutyloxy)-2-{2-[3-(4-methoxyphenyl)-4-oxo-3,4-dihydroquinazolin-2-yl]ethyl}-1H-isoindole-1,3(2H)-dione,
2-{2-[3-(4-methoxyphenyl)-7-methyl-4-oxo-3,4-dihydropyrido[2,3-d]pyrimidin-2-yl]ethyl}-4-(2,2,2-trifluoroethoxy)-1H-isoindole-1,3(2H)-dione
4-methoxy-2-{2-[3-(1-methyl-1H-indazol-6-yl)-4-oxo-3,4-dihydroquinazolin-2-yl]ethyl}-1H-isoindole-1,3(2H)-dione,
2-{2-(3-(4-methoxyphenyl)-7-methyl-4-oxo-3,4-dihydropyrido[2,3-d]pyrimidin-2-yl]ethyl}-4-(propan-2-yloxy)-1H-isoindole-1,3(2H)-dione
2-[2-(3-cyclohexyl-4-oxo-3,4-dihydroquinazolin-2-yl)ethyl]-4-(propan-2-yloxy)-1H-isoindole-1,3(2H)-dione
2-{2-[3-(4-methoxyphenyl)-4-oxo-3,4-dihydroquinazolin-2-yl]ethyl}-1H-isoindole-1,3(2H)-dione
4-hydroxy-2-{2-[3-(4-methoxyphenyl)-4-oxo-3,4-dihydroquinazolin-2-yl]ethyl}-1H-isoindole-1,3(2H)-dione,
4-methoxy-2-{2-[3-(4-methoxyphenyl)-4-oxo-3,4-dihydroquinazolin-2-yl]ethyl}-1H-isoindole-1,3(2H)-dione,
2-{2-[3-(4-methoxyphenyl)-4-oxo-3,4-dihydroquinazolin-2-yl]ethyl}-4-(1,3-oxazol-2-yl)-1H-isoindole-1,3(2H)-dione,
2-(2-{3-[4-(benzyloxy)phenyl]-4-oxo-3,4-dihydroquinazolin-2-yl}ethyl)-4-isopropoxy-1H-isoindole-1,3(2H)-dione
2-{2-[3-(4-hydroxyphenyl)-4-oxo-3,4-dihydroquinazolin-2-yl]ethyl}-4-isopropoxy-1H-isoindole-1,3(2H)-dione 4-isopropoxy-2-{2-[3-(4-methoxyphenyl)-4-oxo-3,4-dihydroquinazolin-2-yl]ethyl}-1H-isoindole-1,3(2H)-dione,
2-methoxy-N-{2-[3-(4-methoxyphenyl)-4-oxo-3,4-dihydroquinazolin-2-yl]ethyl}-benzamide,
2-{2-[3-(1H-indazol-6-yl)-7-methyl-4-oxo-3,4-dihydroquinazolin-2-yl]ethyl}-4-(propan-2-yloxy)-1H-isoindole-1,3(2H)-dione,
2-{2-[7-methyl-3-(1-methyl-1H-indazol-6-yl)-4-oxo-3,4-dihydroquinazolin-2-yl]ethyl}-4-(propan-2-yloxy)-1H-isoindole-1,3(2H)-dione,
or a pharmaceutically acceptable salts thereof wherein the radiolabeled compound is radiolabeled with $^{11}$C or $^{18}$F.

2. A compound which is 4-isopropoxy-2-{2-[3-(4-$^{11}$C-methoxyphenyl)-4-oxo-3,4-dihydroquinazolin-2-yl]ethyl}-1H-isoindole-1,3(2H)-dione or a pharmaceutically acceptable salt thereof.

3. A compound which is 2-{2-[7-methyl-3-(1-$^{11}$C-methyl-1H-indazol-6-yl)-4-oxo-3,4-dihydroquinazolin-2-yl]ethyl}-4-(propan-2-yloxy)-1H-isoindole-1,3(2H)dione, or a pharmaceutically acceptable salt thereof.

4. A method for quantitative imaging of PDE10 in a mammal which comprises administering to a human in need of such imaging an effective amount of a radiolabeled compound selected from:
2-{2-[3-(4-methoxyphenyl)-4-oxo-3,4-dihydropyrido[2,3-d]pyrimidin-2-yl]ethyl}-1H-isoindole-1,3(2H)-dione,
2-[2-(3-biphenyl-3-yl-4-oxo-3,4-dihydroquinazolin-2-yl)ethyl]-1H-isoindole-1,3(2H)-dione,
2-{2-[7-chloro-3-(4-methylphenyl)-4-oxo-3,4-dihydroquinazolin-2-yl]ethyl}-1H-isoindole-1,3(2H)-dione,
2-{2-[3-(4-methoxyphenyl)-4-oxo-3,4-dihydroquinazolin-2-yl]ethyl}-4-methyl-1H-isoindole-1,3(2H)-dione,
2-{2-[3-(4-methoxyphenyl)-4-oxo-3,4-dihydroquinazolin-2-yl]ethyl}-5-methyl-1H-isoindole-1,3(2H)-dione,
2-{2-[3-(4-methoxyphenyl)-4-oxo-3,4-dihydroquinazolin-2-yl]ethyl}-1,3-dioxoisoindoline-4-carbonitrile,
4-methoxy-2-{2-[7-methoxy-3-(3-methylphenyl)-4-oxo-3,4-dihydroquinazolin-2-yl]ethyl}-1H-isoindole-1,3(2H)-dione,
4-methoxy-2-{2-[3-(4-methoxyphenyl)-7-methyl-4-oxo-3,4-dihydroquinazolin-2-yl]ethyl}-1H-isoindole-1,3(2H)-dione,
tert-butyl 3-{2-[3-(4-methoxyphenyl)-4-oxo-3,4-dihydroquinazolin-2-yl]ethyl}-1H-indole-1-carboxylate,
N-biphenyl-2-yl-N'-{2-[3-(4-methoxyphenyl)-4-oxo-3,4-dihydroquinazolin-2-yl]ethyl}urea,
4-isopropoxy-2-{2-[3-(4-methoxyphenyl)-4-oxo-3,4-dihydropyrido[2,3-d]pyrimidin-2-yl]ethyl}-1H-isoindole-1,3(2H)-dione,
2-(2-{3-[4-(2-fluoroethoxy)phenyl]-4-oxo-3,4-dihydroquinazolin-2-yl}ethyl)-4-isopropoxy-1H-isoindole-1,3(2H)-dione,
2-{2-[3-(1H-indol-6-yl)-7-methoxy-4-oxo-3,4-dihydroquinazolin-2-yl]ethyl}-4-isopropoxy-1H-isoindole-1,3(2H)-dione,
4-isopropoxy-2-{2-[7-methoxy-3-(3-methylphenyl)-4-oxo-3,4-dihydroquinazolin-2-yl]ethyl}-1H-isoindole-1,3(2H)-dione,
2-{2-[3-(1H-indazol-6-yl)-4-oxo-3,4-dihydropyrido[2,3-d]pyrimidin-2-yl]ethyl}-4-isopropoxy-1H-isoindole-1,3(2H)-dione,
2-{2-[3-(4-methoxyphenyl)-4-oxo-3,4-dihydroquinazolin-2-yl]ethyl}-4-pyridin-4-yl-1H-isoindole-1,3(2H)-dione, 2-{[3-(4-methoxyphenyl)-4-oxo-3,4-dihydroquinazolin-2-yl]methyl}-1H-isoindole-1,3(2H)-dione,
2-{3-[3-(4-methoxyphenyl)-4-oxo-3,4-dihydroquinazolin-2-yl]propyl}-1H-isoindole-1,3(2H)-dione,
2-{3-[3-(4-methoxyphenyl)-4-oxo-3,4-dihydroquinazolin-2-yl]ethyl}-4-(2,2,2-trifluoroethoxy)-1H-isoindole-1,3(2H)-dione,
4-(cyclopropylmethoxy)-2-{2-[3-(4-methoxyphenyl)-4-oxo-3,4-dihydroquinazolin-2-yl]ethyl}-1H-isoindole-1,3(2H)-dione,
4-(cyclobutyloxy)-2-{2-[3-(4-methoxyphenyl)-4-oxo-3,4-dihydroquinazolin-2-yl]ethyl}-1H-isoindole-1,3(2H)-dione,
2-{2-[3-(4-methoxyphenyl)-7-methyl-4-oxo-3,4-dihydropyrido[2,3-d]pyrimidin-2-yl]ethyl}-4-(2,2,2-trifluoroethoxy)-1H-isoindole-1,3(2H)-dione
4-methoxy-2-{2-[3-(1-methyl-1H-indazol-6-yl)-4-oxo-3,4-dihydroquinazolin-2-yl]ethyl}-1H-isoindole-1,3(2H)-dione,
2-{2-[3-(4-methoxyphenyl)-7-methyl-4-oxo-3,4-dihydropyrido[2,3-d]pyrimidin-2-yl]ethyl}-4-(propan-2-yloxy)-1H-isoindole-1,3(2H)-dione
2-[2-(3-cyclohexyl-4-oxo-3,4-dihydroquinazolin-2-yl)ethyl]-4-(propan-2-yloxy)-1H-isoindole-1,3(2H)-dione
2-{2-[3-(4-methoxyphenyl)-4-oxo-3,4-dihydroquinazolin-2-yl]ethyl}-1H-isoindole-1,3(2H)-dione
4-hydroxy-2-{2-[3-(4-methoxyphenyl)-4-oxo-3,4-dihydroquinazolin-2-yl]ethyl}-1H-isoindole-1,3(2H)-dione,
4-methoxy-2-{2-[3-(4-methoxyphenyl)-4-oxo-3,4-dihydroquinazolin-2-yl]ethyl}-1H-isoindole-1,3(2H)-dione,
2-{2-[3-(4-methoxyphenyl)-4-oxo-3,4-dihydroquinazolin-2-yl]ethyl}-4-(1,3-oxazol-2-yl)-1H-isoindole-1,3(2H)-dione,
2-(2-{3-[4-(benzyloxy)phenyl]-4-oxo-3,4-dihydroquinazolin-2-yl}ethyl)-4-isopropoxy-1H-isoindole-1,3(2H)-dione
2-{2-[3-(4-hydroxyphenyl)-4-oxo-3,4-dihydroquinazolin-2-yl]ethyl}-4-isopropoxy-1H-isoindole-1,3(2H)-dione
4-isopropoxy-2-{2-[3-(4-methoxyphenyl)-4-oxo-3,4-dihydroquinazolin-2-yl]ethyl}-1H-isoindole-1,3(2H)-dione,
2-methoxy-N-{2-[3-(4-methoxyphenyl)-4-oxo-3,4-dihydroquinazolin-2-yl]ethyl}-benzamide,
2-{2-[3-(1H-indazol-6-yl)-7-methyl-4-oxo-3,4-dihydroquinazolin-2-yl]ethyl}-4-(propan-2-yloxy)-1H-isoindole-1,3(2H)-dione, and
2-{2-[7-methyl-3-(1-methyl-1H-indazol-6-yl)-4-oxo-3,4-dihydroquinazolin-2-yl]ethyl}-4-(propan-2-yloxy)-1H-isoindole-1,3(2H)-dione, or a pharmaceutically acceptable salt thereof, imaging the human, obtaining an image useful for quantifying PDE10 in the brain of the mammal using positron emission tomography wherein the radiolabeled compound is radiolabeled with $^{11}$C or $^{18}$F.

5. A method for diagnostic imaging of a neurological or psychiatric disorder associated with PDE10 dysfunction, striatal hypofunction or basal ganglia dysfunction in a mammal which comprises administering to a human in need of such diagnostic imaging an effective amount of a radiolabeled compound selected from: 2-{2-[3-(4-methoxyphenyl)-4-oxo-3,4-dihydropyrido[2,3-d]pyrimidin-2-yl]ethyl}-1H-isoindole-1,3(2H)-dione,
2-[2-(3-biphenyl-3-yl-4-oxo-3,4-dihydroquinazolin-2-yl)ethyl]-1H-isoindole-1,3(2H)-dione,
2-{2-[7-chloro-3-(4-methylphenyl)-4-oxo-3,4-dihydroquinazolin-2-yl]ethyl}-1H-isoindole-1,3(2H)-dione,
2-{2-[3-(4-methoxyphenyl)-4-oxo-3,4-dihydroquinazolin-2-yl]ethyl}-4-methyl-1H-isoindole-1,3(2H)-dione,
2-{2-[3-(4-methoxyphenyl)-4-oxo-3,4-dihydroquinazolin-2-yl]ethyl}-5-methyl-1H-isoindole-1,3(2H)-dione,
2-{2-[3-(4-methoxyphenyl)-4-oxo-3,4-dihydroquinazolin-2-yl]ethyl}-1,3-dioxoisoindoline-4-carbonitrile,
4-methoxy-2-{2-[7-methoxy-3-(3-methylphenyl)-4-oxo-3,4-dihydroquinazolin-2-yl]ethyl}-1H-isoindole-1,3(2H)-dione,
4-methoxy-2-{2-[3-(4-methoxyphenyl)-7-methyl-4-oxo-3,4-dihydroquinazolin-2-yl]ethyl}-1H-isoindole-1,3(2H)-dione,
tert-butyl 3-{2-[3-(4-methoxyphenyl)-4-oxo-3,4-dihydroquinazolin-2-yl]ethyl}-1H-indole-1-carboxylate,
N-biphenyl-2-yl-N'-{2-[3-(4-methoxyphenyl)-4-oxo-3,4-dihydroquinazolin-2-yl]ethyl}urea,
4-isopropoxy-2-{2-[3-(4-methoxyphenyl)-4-oxo-3,4-dihydropyrido[2,3-d]pyrimidin-2-yl]ethyl}-1H-isoindole-1,3(2H)-dione,
2-(2-{3-[4-(2-fluoroethoxy)phenyl]-4-oxo-3,4-dihydroquinazolin-2-yl}ethyl)-4-isopropoxy-1H-isoindole-1,3(2H)-dione,
2-{2-[3-(1H-indol-6-yl)-7-methoxy-4-oxo-3,4-dihydroquinazolin-2-yl]ethyl}-4-isopropoxy-1H-isoindole-1,3(2H)-dione,
4-isopropoxy-2-{2-[7-methoxy-3-(3-methylphenyl)-4-oxo-3,4-dihydroquinazolin-2-yl]ethyl}-1H-isoindole-1,3(2H)-dione,
2-{2-[3-(1H-indazol-6-yl)-4-oxo-3,4-dihydropyrido[2,3-d]pyrimidin-2-yl]ethyl}-4-isopropoxy-1H-isoindole-1,3(2H)-dione,
2-{2-[3-(4-methoxyphenyl)-4-oxo-3,4-dihydroquinazolin-2-yl]ethyl}-4-pyridin-4-yl-1H-isoindole-1,3(2H)-dione,
2-{[3-(4-methoxyphenyl)-4-oxo-3,4-dihydroquinazolin-2-yl]methyl}-1H-isoindole-1,3(2H)-dione,
2-{3-[3-(4-methoxyphenyl)-4-oxo-3,4-dihydroquinazolin-2-yl]propyl}-1H-isoindole-1,3(2H)-dione,
2-{3-[3-(4-methoxyphenyl)-4-oxo-3,4-dihydroquinazolin-2-yl]ethyl}-4-(2,2,2-trifluoroethoxy)-1H-isoindole-1,3(2H)-dione,
4-(cyclopropylmethoxy)-2-{2-[3-(4-methoxyphenyl)-4-oxo-3,4-dihydroquinazolin-2-yl]ethyl}-1H-isoindole-1,3(2H)-dione,
4-(cyclobutyloxy)-2-{2-[3-(4-methoxyphenyl)-4-oxo-3,4-dihydroquinazolin-2-yl]ethyl}-1H-isoindole-1,3(2H)-dione,
2-{2-[3-(4-methoxyphenyl)-7-methyl-4-oxo-3,4-dihydropyrido[2,3-d]pyrimidin-2-yl]ethyl}-4-(2,2,2-trifluoroethoxy)-1H-isoindole-1,3(2H)-dione
4-methoxy-2-{2-[3-(1-methyl-1H-indazol-6-yl)-4-oxo-3,4-dihydroquinazolin-2-yl]ethyl}-1H-isoindole-1,3(2H)-dione,
2-{2-[3-(4-methoxyphenyl)-7-methyl-4-oxo-3,4-dihydropyrido[2,3-d]pyrimidin-2-yl]ethyl}-4-(propan-2-yloxy)-1H-isoindole-1,3(2H)-dione
2-[2-(3-cyclohexyl-4-oxo-3,4-dihydroquinazolin-2-yl)ethyl]-4-(propan-2-yloxy)-1H-isoindole-1,3(2H)-dione
2-{2-[3-(4-methoxyphenyl)-4-oxo-3,4-dihydroquinazolin-2-yl]ethyl}-1H-isoindole-1,3(2H)-dione
4-hydroxy-2-{2-[3-(4-methoxyphenyl)-4-oxo-3,4-dihydroquinazolin-2-yl]ethyl}-1H-isoindole-1,3(2H)-dione,
4-methoxy-2-{2-[3-(4-methoxyphenyl)-4-oxo-3,4-dihydroquinazolin-2-yl]ethyl}-1H-isoindole-1,3(2H)-dione,
2-{2-[3-(4-methoxyphenyl)-4-oxo-3,4-dihydroquinazolin-2-yl]ethyl}-4(1,3-oxazol-2-yl)-1H-isoindole-1,3(2H)-dione, 2-(2-{3-[4-(benzyloxy)phenyl]-4-oxo-3,4-dihydroquinazolin-2-yl}ethyl)-4-isopropoxy-1H-isoindole-1,3(2H)-dione
2-{2-[3-(4-hydroxyphenyl)-4-oxo-3,4-dihydroquinazolin-2-yl]ethyl}-4-isopropoxy-1H-isoindole-1,3(2H)-dione
4-isopropoxy-2-{2-[3-(4-methoxyphenyl)-4-oxo-3,4-dihydroquinazolin-2-yl]ethyl}-1H-isoindole-1,3(2H)-dione,
2-methoxy-N-{2-[3-(4-methoxyphenyl)-4-oxo-3,4-dihydroquinazolin-2-yl]ethyl}-benzamide,
2-{2-[3-(1H-indazol-6-yl)-7-methyl-4-oxo-3,4-dihydroquinazolin-2-yl]ethyl}-4-(propan-2-yloxy)-1H-isoindole-1,3(2H)-dione, and
2-{2-[7-methyl-3-(1-methyl-1H-indazol-6-yl)-4-oxo-3,4-dihydroquinazolin-2-yl]ethyl}-4-(propan-2-yloxy)-1H-isoindole-1,3(2H)-dione, or a pharmaceutically acceptable salt thereof, imaging the human, obtaining an image useful for quantifying PDE10 in the brain of the mammal using positron emission tomography and quantifying PDE10 in the brain wherein the radiolabeled compound is radiolabeled with $^{11}C$ or $^{18}F$.

6. A method for the quantification of PDE10 in mammalian tissue which comprises contacting such mammalian tissue in which quantification is desired with an effective amount of a radiolabeled compound selected from: 2-{2-[3-(4-methoxyphenyl)-4-oxo-3,4-dihydropyrido[2,3-d]pyrimidin-2-yl]ethyl}-1H-isoindole-1,3(2H)-dione, 2-[2-(3-biphenyl-3-yl-4-oxo-3,4-dihydroquinazolin-2-yl)ethyl]-1H-isoindole-1,3(2H)-dione,
2-{2-[7-chloro-3-(4-methylphenyl)-4-oxo-3,4-dihydroquinazolin-2-yl]ethyl}-1H-isoindole-1,3(2H)-dione,
2-{2-[3-(4-methoxyphenyl)-4-oxo-3,4-dihydroquinazolin-2-yl]ethyl}-4-methyl-1H-isoindole-1,3(2H)-dione,
2-{2-[3-(4-methoxyphenyl)-4-oxo-3,4-dihydroquinazolin-2-yl]ethyl}-5-methyl-1H-isoindole-1,3(2H)-dione,
2-{2-[3-(4-methoxyphenyl)-4-oxo-3,4-dihydroquinazolin-2-yl]ethyl}-1,3-dioxoisoindoline-4-carbonitrile,
4-methoxy-2-{2-[7-methoxy-3-(3-methylphenyl)-4-oxo-3,4-dihydroquinazolin-2-yl]ethyl}-1H-isoindole-1,3(2H)-dione,
4-methoxy-2-{2-[3-(4-methoxyphenyl)-7-methyl-4-oxo-3,4-dihydroquinazolin-2-yl]ethyl}-1H-isoindole-1,3(2H)-dione,
tert-butyl 3-{2-[3-(4-methoxyphenyl)-4-oxo-3,4-dihydroquinazolin-2-yl]ethyl}-1H-indole-1-carboxylate,
N-biphenyl-2-yl-N'-{2-[3-(4-methoxyphenyl)-4-oxo-3,4-dihydroquinazolin-2-yl]ethyl}urea,
4-isopropoxy-2-{2-[3-(4-methoxyphenyl)-4-oxo-3,4-dihydropyrido[2,3-d]pyrimidin-2-yl]ethyl}-1H-isoindole-1,3(2H)-dione,
2-(2-{3-[4-(2-fluoroethoxy)phenyl]-4-oxo-3,4-dihydroquinazolin-2-yl}ethyl)-4-isopropoxy-1H-isoindole-1,3(2H)-dione,
2-{2-[3-(1H-indol-6-yl)-7-methoxy-4-oxo-3,4-dihydroquinazolin-2-yl]ethyl}-4-isopropoxy-1H-isoindole-1,3(2H)-dione,
4-isopropoxy-2-{2-[7-methoxy-3-(3-methylphenyl)-4-oxo-3,4-dihydroquinazolin-2-yl]ethyl}-1H-isoindole-1,3(2H)-dione,
2-{2-[3-(1H-indazol-6-yl)-4-oxo-3,4-dihydropyrido[2,3-d]pyrimidin-2-yl]ethyl}-4-isopropoxy-1H-isoindole-1,3(2H)-dione,
2-{2-[3-(4-methoxyphenyl)-4-oxo-3,4-dihydroquinazolin-2-yl]ethyl}-4-pyridin-4-yl-1H-isoindole-1,3(2H)-dione,
2-{[3-(4-methoxyphenyl)-4-oxo-3,4-dihydroquinazolin-2-yl]methyl}-1H-isoindole-1,3(2H)-dione,
2-{3-[3-(4-methoxyphenyl)-4-oxo-3,4-dihydroquinazolin-2-yl]propyl}-1H-isoindole-1,3(2H)-dione,
2-{3-[3-(4-methoxyphenyl)-4-oxo-3,4-dihydroquinazolin-2-yl]ethyl}-4-(2,2,2-trifluoroethoxy)-1H-isoindole-1,3(2H)-dione,
4-(cyclopropylmethoxy)-2-{2-[3-(4-methoxyphenyl)-4-oxo-3,4-dihydroquinazolin-2-yl]ethyl}-1H-isoindole-1,3(2H)-dione,
4-(cyclobutyloxy)-2-{2-[3-(4-methoxyphenyl)-4-oxo-3,4-dihydroquinazolin-2-yl]ethyl}-1H-isoindole-1,3(2H)-dione,
2-{2-[3-(4-methoxyphenyl)-7-methyl-4-oxo-3,4-dihydropyrido[2,3-d]pyrimidin-2-yl]ethyl}-4-(2,2,2-trifluoroethoxy)-1H-isoindole-1,3(2H)-dione
4-methoxy-2-{2-[3-(1-methyl-1H-indazol-6-yl)-4-oxo-3,4-dihydroquinazolin-2-yl]ethyl}-1H-isoindole-1,3(2H)-dione,
2-{2-(3-(4-methoxyphenyl)-7-methyl-4-oxo-3,4-dihydropyrido[2,3-d]pyrimidin-2-yl]ethyl}-4-(propan-2-yloxy)-1H-isoindole-1,3(2H)-dione
2-[2-(3-cyclohexyl-4-oxo-3,4-dihydroquinazolin-2-yl)ethyl]-4-(propan-2-yloxy)-1H-isoindole-1,3(2H)-dione
2-{2-[3-(4-methoxyphenyl)-4-oxo-3,4-dihydroquinazolin-2-yl]ethyl}-1H-isoindole-1,3(2H)-dione
2-{2-[3-(4-methoxyphenyl)-4-oxo-3,4-dihydroquinazolin-2-yl]ethyl}-1H-isoindole-1,3(2H)-dione,
4-hydroxy-2-{2-[3-(4-methoxyphenyl)-4-oxo-3,4-dihydroquinazolin-2-yl]ethyl}-1H-isoindole-1,3(2H)-dione,
4-methoxy-2-{2-[3-(4-methoxyphenyl)-4-oxo-3,4-dihydroquinazolin-2-yl]ethyl}-1H-isoindole-1,3(2H)-dione,
2-{2-[3-(4-methoxyphenyl)-4-oxo-3,4-dihydroquinazolin-2-yl]ethyl}-4-(1,3-oxazol-2-yl)-1H-isoindole-1,3(2H)-dione,
2-(2-{3-[4-(benzyloxy)phenyl]-4-oxo-3,4-dihydroquinazolin-2-yl}ethyl)-4-isopropoxy-1H-isoindole-1,3(2H)-dione
2-{2-[3-(4-hydroxyphenyl)-4-oxo-3,4-dihydroquinazolin-2-yl]ethyl}-4-isopropoxy-1H-isoindole-1,3(2H)-dione
4-isopropoxy-2-{2-[3-(4-methoxyphenyl)-4-oxo-3,4-dihydroquinazolin-2-yl]ethyl}-1H-isoindole-1,3(2H)-dione,
2-methoxy-N-{2-[3-(4-methoxyphenyl)-4-oxo-3,4-dihydroquinazolin-2-yl]ethyl}-benzamide,
2-{2-[3-(1H-indazol-6-yl)-7-methyl-4-oxo-3,4-dihydroquinazolin-2-yl]ethyl}-4-(propan-2-yloxy)-1H-isoindole-1,3(2H)-dione, and
2-{2-[7-methyl-3-(1-methyl-1H-indazol-6-yl)-4-oxo-3,4-dihydroquinazolin-2-yl]ethyl}-4-(propan-2-yloxy)-1H-isoindole-1,3(2H)-dione, or a pharmaceutically acceptable salt thereof, imaging the human, obtaining an image useful for quantifying PDE10 in the brain of the mammal using positron emission tomography and quantifying PDE10 in the brain wherein the radiolabeled compound is radiolabeled with $^{11}C$ or $^{18}F$.

* * * * *